United States Patent
Watanabe et al.

(10) Patent No.: US 9,499,483 B2
(45) Date of Patent: Nov. 22, 2016

(54) CRYSTAL OF PYRROLE DERIVATIVE AND METHOD FOR PRODUCING THE SAME

(71) Applicant: Daiichi Sankyo Company, Limited, Chuo-ku, Tokyo (JP)

(72) Inventors: Masashi Watanabe, Tokyo (JP); Takahiro Okachi, Kanagawa (JP); Michiaki Kawahara, Tokyo (JP); Hiroshi Nagasawa, Kanagawa (JP); Noritada Sato, Kanagawa (JP); Takashi Takita, Kanagawa (JP); Gen Hasegawa, Kanagawa (JP)

(73) Assignee: Daiichi Sankyo Company, Limited, Chuo-ku (JP)

(*) Notice: Subject to any disclaimer, the term of this patent is extended or adjusted under 35 U.S.C. 154(b) by 0 days.

(21) Appl. No.: 14/879,814

(22) Filed: Oct. 9, 2015

(65) Prior Publication Data

US 2016/0096803 A1  Apr. 7, 2016

Related U.S. Application Data

(63) Continuation-in-part of application No. PCT/JP2014/060055, filed on Apr. 7, 2014.

(30) Foreign Application Priority Data

Apr. 10, 2013  (JP) ................. 2013-081879

(51) Int. Cl.
| | |
|---|---|
| C07D 207/34 | (2006.01) |
| A61K 9/00 | (2006.01) |
| A61K 9/20 | (2006.01) |
| A61K 9/48 | (2006.01) |
| C07D 471/08 | (2006.01) |

(52) U.S. Cl.
CPC ........... *C07D 207/34* (2013.01); *A61K 9/0095* (2013.01); *A61K 9/2018* (2013.01); *A61K 9/4858* (2013.01); *C07D 471/08* (2013.01)

(58) Field of Classification Search
None
See application file for complete search history.

(56) References Cited

U.S. PATENT DOCUMENTS

| | | |
|---|---|---|
| 6,939,968 B2 | 9/2005 | Vrudhula |
| 8,026,237 B2 | 9/2011 | Canne Bannen |
| 8,754,118 B2 | 6/2014 | Aoki |

FOREIGN PATENT DOCUMENTS

| | | |
|---|---|---|
| EP | 0 934 934 A2 | 8/1999 |
| JP | 11-279158 A | 10/1999 |
| JP | 2006-512378 A | 4/2006 |
| JP | 2008-508308 A | 3/2008 |
| JP | 2010-111657 A | 5/2010 |
| WO | 2008/126831 A1 | 10/2008 |
| WO | 2010/098286 A1 | 9/2010 |

OTHER PUBLICATIONS

International Preliminary Report on Patentability mailed Oct. 13, 2015, issued in International Application No. PCT/JP2014/060055, filed Apr. 7, 2014, 14 pages.
International Search Report and Written Opinion mailed May 20, 2014, issued in International Application No. PCT/JP2014/060055, filed Apr. 7, 2014, 9 pages.
Nohira, H., "4. Optical Resolution by Diastereomeric Salt Formation," Quarterly Journal of Chemical Review, No. 6, 1989, in "Resolution of Optical Isomers," Japan Scientific Societies Press, Tokyo, Jun. 10, 1999, pp. 45-54.
First Office Action, mailed Jul. 13, 2016, in corresponding Chinese Application No. 2014800205226, filed Apr. 7, 2014, 11 pages.

*Primary Examiner* — Rebecca Anderson
*Assistant Examiner* — Po-Chih Chen
(74) *Attorney, Agent, or Firm* — Christensen O'Connor Johnson Kindness PLLC

(57) ABSTRACT

The present invention provides a production intermediate of an atropisomer of a pyrrole derivative having excellent mineralocorticoid receptor antagonistic activity, a method for producing the same, and a crystal thereof. A method for producing an atropisomer of a pyrrole derivative including a step of resolving a compound represented by the following general formula (I) [wherein $R^1$ represents a methyl group or a trifluoromethyl group, $R^2$ represents a hydrogen atom or a C1-C3 alkoxy group, and n represents an integer selected from 1 to 3] into its atropisomers, characterized by using an optically active amine having a cinchonine skeletal formula, and a crystal of (S)-1-(2-hydroxyethyl)-4-methyl-N-[4-(methylsulfonyl)phenyl]-5-[2-(trifluoromethyl)phenyl]-1H-pyrrole-3-carboxamide.

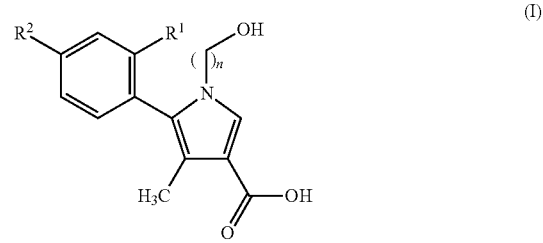

(I)

5 Claims, 2 Drawing Sheets

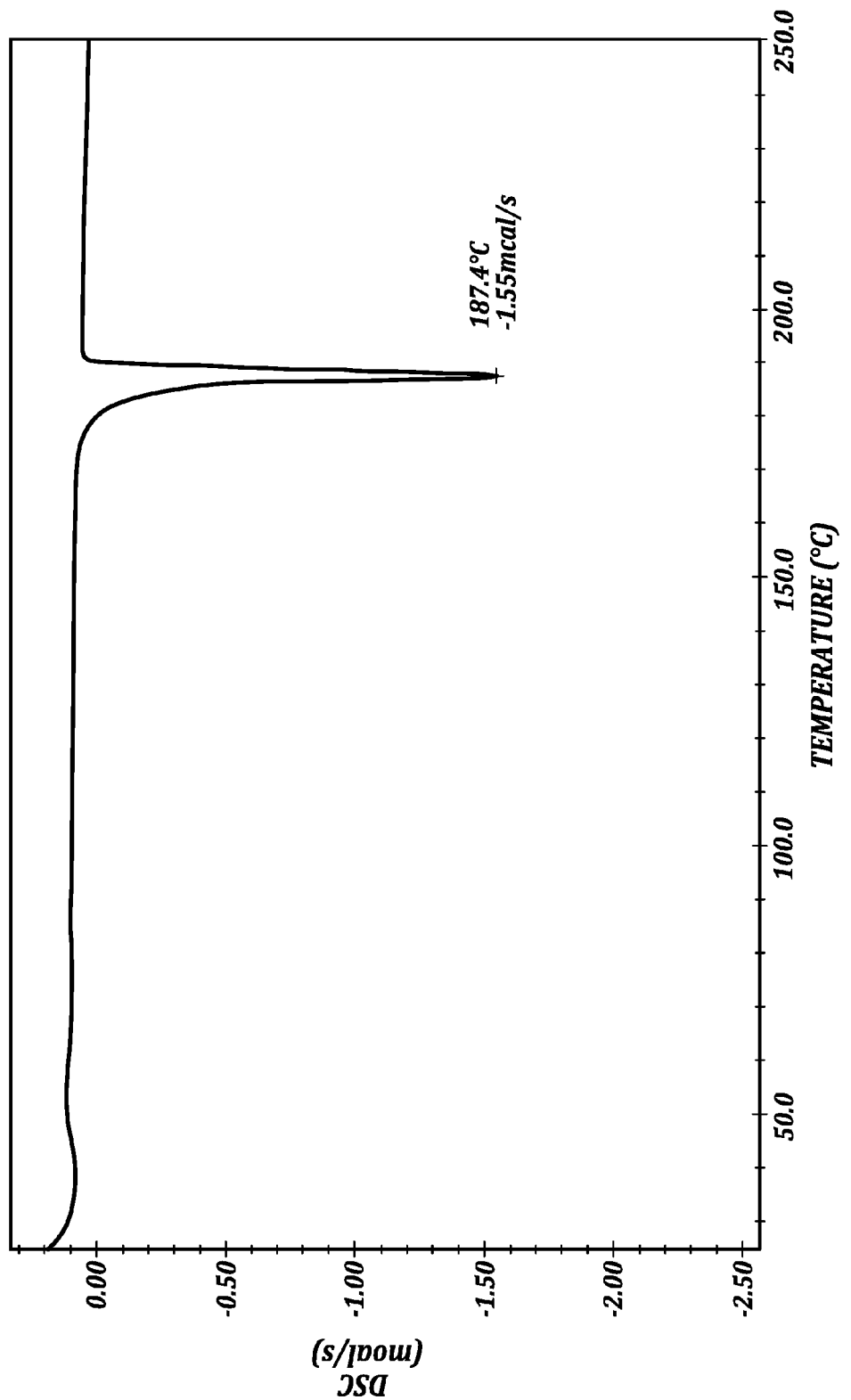

CRYSTAL OF PYRROLE DERIVATIVE AND METHOD FOR PRODUCING THE SAME

TECHNICAL FIELD

The present invention relates to a crystal of an atropisomer of a pyrrole derivative having excellent mineralocorticoid receptor antagonistic activity, a method for producing the same, and a production intermediate thereof.

BACKGROUND ART

The mineralocorticoid receptor (MR) (aldosterone receptor) is known to play an important role in regulating electrolyte balance and blood pressure in the body. For example, MR antagonists such as spironolactone and eplerenone, both of which have a steroidal structure, are known to be useful for the treatment of hypertension and heart failure.

A pyrrole derivative having excellent mineralocorticoid receptor antagonistic activity is disclosed in PTL 1 and PTL 2 and is known to be useful for the treatment of hypertension, angina pectoris, acute coronary syndrome, congestive heart failure, nephropathy, arteriosclerosis, cerebral infarction, fibrosis, primary aldosteronism, or a heart disease (particularly, hypertension or diabetic nephropathy).

CITATION LIST

Patent Literature

PTL 1: WO 2006/012642 (US Publication No. US 2008-0234270)
PTL 2: WO 2008/056907 (US Publication No. US 2010-0093826)

SUMMARY OF INVENTION

Technical Problem

A substance to be used for a pharmaceutical product is required to have strictly high purity so as not to cause unpredicted side effects (for example, toxicity, etc.) due to its impurities. Further, in its industrial production method (mass production method), impurities are required to be removed by a simpler operation.

In addition, it is important that a pharmaceutical drug substance can be stored for a long period of time while maintaining its quality. In the case where it is necessary to store a pharmaceutical drug substance under low temperature conditions, a large-scale refrigeration facility is needed for maintaining quality, and therefore, it is industrially meaningful to find a stable crystal which can be stored at room temperature or higher.

Under such circumstances, the present inventors made intensive studies for developing a method for producing a pyrrole derivative having excellent MR antagonistic activity with higher quality in higher yield by using a more industrially advantageous operation method with lower environmental impact. As a result, they found a method for efficient resolution of an atropisomer of a novel synthetic intermediate, and based on this finding, they established a method for producing a pyrrole derivative with high quality in high yield by using an industrially advantageous operation, and thus completed the present invention.

Solution to Problem

The present inventors intensively studied a crystal of an atropisomer of a pyrrole derivative, a production intermediate thereof, and an efficient method for producing the same so as to improve solubility, purity, stability, and the like for enhancing the medical usefulness of an atropisomer of a pyrrole derivative having excellent mineralocorticoid receptor antagonistic activity.

Hereinafter, the present invention will be described in detail.

The present invention is directed to:

(1) a method for resolving a compound represented by the following general formula (I):

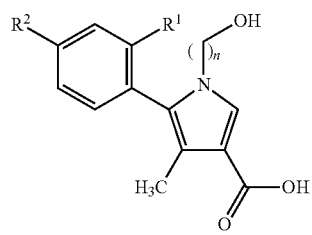

(I)

[wherein $R^1$ represents a methyl group or a trifluoromethyl group, $R^2$ represents a hydrogen atom or a C1-C3 alkoxy group, and n represents an integer selected from 1 to 3] into its atropisomers, characterized by using an optically active amine having a cinchonine skeletal formula;

(2) the method according to the above (1), wherein the optically active amine is one compound selected from the group of compounds represented by the following formulae:

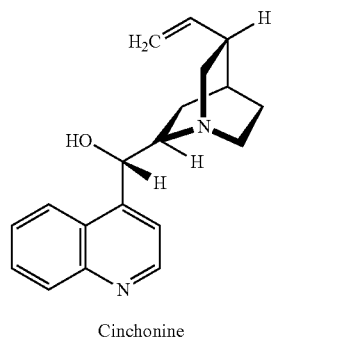

Cinchonine

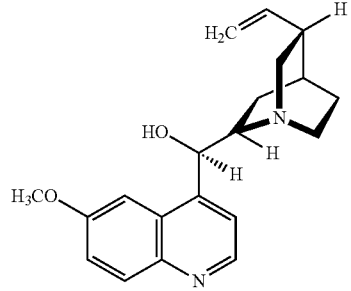

Quinine

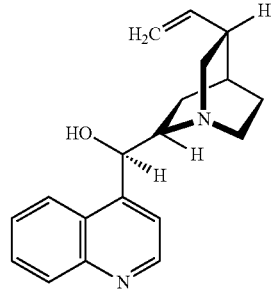

Cinchonidine

-continued

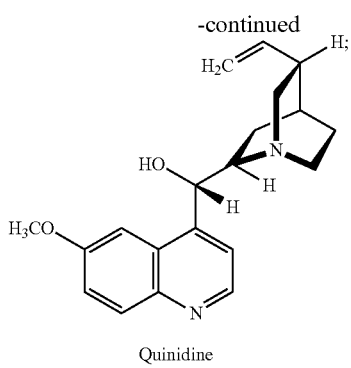
Quinidine (3) the method according to the above (1), wherein the optically active amine is quinine represented by the following formula:

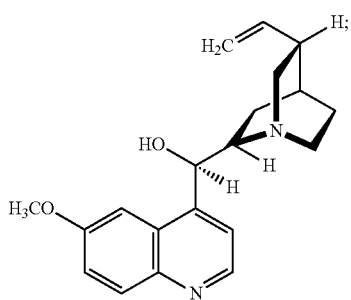

(4) the method according to any one of the above (1) to (3), wherein the method is performed in an organic solvent or a mixed solvent of an organic solvent and water;

(5) the method according to any one of the above (1) to (4), wherein the compound represented by the general formula (I) is the following compound (Ia):

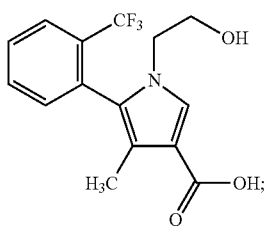
(Ia)

(6) a method for producing (S)-1-(2-hydroxyethyl)-4-methyl-N-[4-(methylsulfonyl)phenyl]-5-[2-(trifluoromethyl)phenyl]-1H-pyrrole-3-carboxamide represented by the following formula (A):

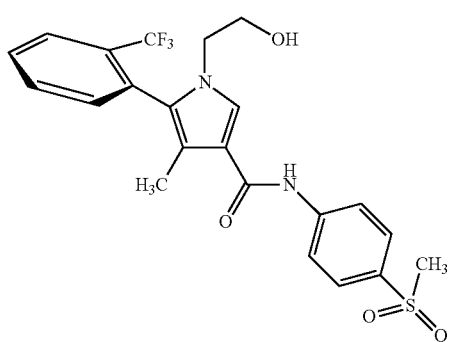
(A)

characterized by obtaining one atropisomer of (RS)-1-(2-hydroxyethyl)-4-methyl-5-[2-(trifluoromethyl)phenyl]-1H-pyrrole-3-carboxylic acid represented by the following formula (Ia):

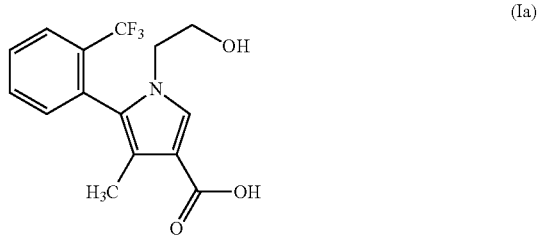 [SMILES: Cc1c(C(=O)O)cn(CCO)c1-c1ccccc1C(F)(F)F]
(Ia)

by resolution using an optically active amine having a cinchonine skeletal formula, removing the optically active amine under acidic conditions, followed by reaction with oxalyl chloride, thereby forming the following intermediate compound (IIa):

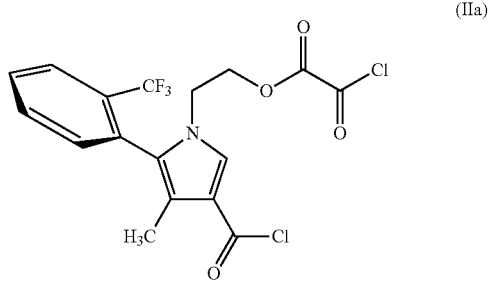
(IIa)

and then further reacting the intermediate compound (IIa) with 4-(methylsulfonyl)aniline, thereby forming the following intermediate compound (IIIa):

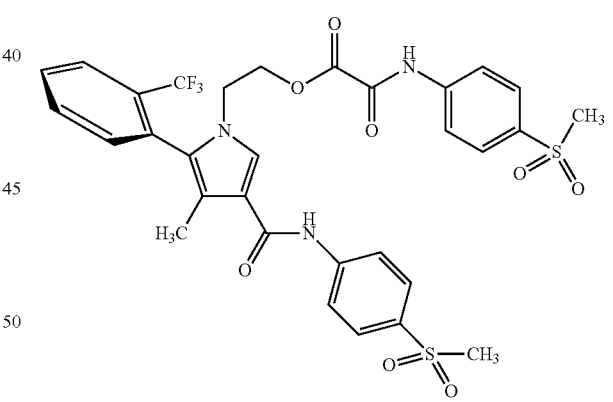
(IIIa)

followed by a base treatment;

(6-1) the production method according to the above (6), wherein the reaction temperature during the reaction with oxalyl chloride for obtaining the intermediate compound (IIa) and during the reaction between the intermediate compound (IIa) and 4-(methylsulfonyl)aniline is 20° C. or lower;

(6-2) the production method according to the above (6), wherein the method includes a step of isolating the intermediate compound (IIIa);

(6-3) the production method according to the above (6), wherein the one atropisomer of (RS)-1-(2-hydroxyethyl)-4-methyl-5-[2-(trifluoromethyl)phenyl]-1H-pyrrole-3-carboxylic acid is (S)-1-(2-hydroxyethyl)-4-methyl-5-[2-(trifluoromethyl)phenyl]-1H-pyrrole-3-carboxylic acid;

(7) (RS)-1-(2-hydroxyethyl)-4-methyl-5-[2-(trifluoromethyl)phenyl]-1H-pyrrole-3-carboxylic acid represented by the following formula (Ia):

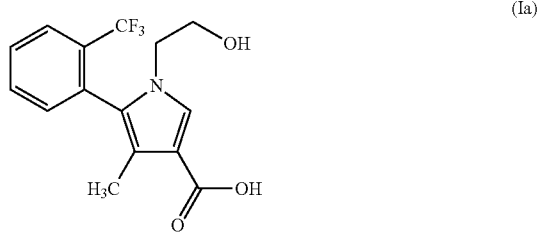 [SMILES: Cc1c(C(=O)O)cn(CCO)c1-c1ccccc1C(F)(F)F]

which is an intermediate for producing (S)-1-(2-hydroxyethyl)-4-methyl-N-[4-(methylsulfonyl)phenyl]-5-[2-(trifluoromethyl)phenyl]-1H-pyrrole-3-carboxamide represented by the following formula (A):

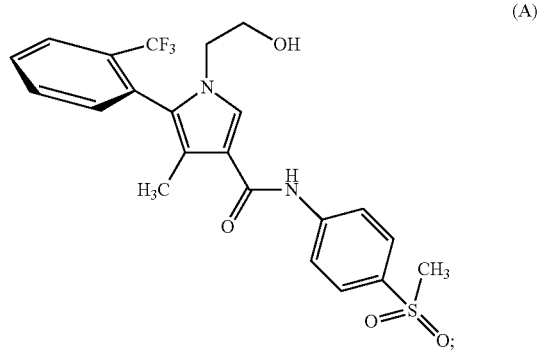

(8) an optically active amine salt (the optically active amine is one compound selected from cinchonine, quinine, cinchonidine, and quinidine) of a compound represented by the following general formula (I):

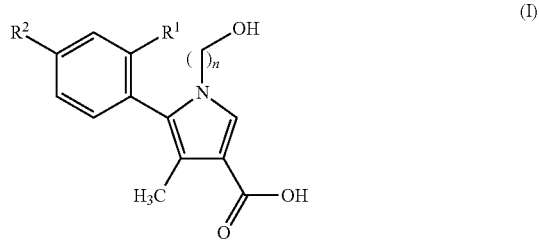

[wherein $R^1$ represents a methyl group or a trifluoromethyl group, $R^2$ represents a hydrogen atom or a C1-C3 alkoxy group, and n represents an integer selected from 1 to 3];

(8-1) (S)-1-(2-hydroxyethyl)-4-methyl-5-[2-(trifluoromethyl)phenyl]-1H-pyrrole-3-carboxylic acid quinine salt;

(9) a crystal of (S)-1-(2-hydroxyethyl)-4-methyl-N-[4-(methylsulfonyl)phenyl]-5-[2-(trifluoromethyl)phenyl]-1H-pyrrole-3-carboxamide represented by the above formula (A), which shows characteristic peaks at diffraction angles 2θ of 6.80, 17.06, 19.24, 22.80, and 25.48 in a powder X-ray diffraction pattern obtained by irradiation with copper Kα radiation (wavelength λ=1.54 Å);

(10) a crystal of (S)-1-(2-hydroxyethyl)-4-methyl-N-[4-(methylsulfonyl)phenyl]-5-[2-(trifluoromethyl)phenyl]-1H-pyrrole-3-carboxamide represented by the above formula (A), which shows main peaks at diffraction angles 2θ of 6.80, 12.32, 13.60, 14.46, 16.30, 17.06, 18.42, 19.24, 19.86, 20.36, 20.82, 21.84, 22.50, 22.80, 23.20, 23.50, 24.60, 24.88, 25.48, 26.96, 27.52, 29.26, 31.80, 32.08, 35.82, 40.32, and 41.36 in a powder X-ray diffraction pattern obtained by irradiation with copper Kα radiation (wavelength λ=1.54 Å);

(10-1) a crystal of (S)-1-(2-hydroxyethyl)-4-methyl-N-[4-(methylsulfonyl)phenyl]-5-[2-(trifluoromethyl)phenyl]-1H-pyrrole-3-carboxamide, which has the X-ray diffraction pattern shown in FIG. 1 in a powder X-ray diffraction pattern obtained by irradiation with copper Kα radiation (wavelength λ=1.54 Å);

(11) a pharmaceutical composition, containing the crystal according to the above (9) or (10) as an active ingredient;

(12) a prophylactic or therapeutic agent for hypertension, angina pectoris, acute coronary syndrome, congestive heart failure, nephropathy, arteriosclerosis, cerebral infarction, fibrosis, primary aldosteronism, or a heart disease, containing the crystal according to the above (9) or (10) as an active ingredient;

(13) a prophylactic or therapeutic agent for hypertension, containing the crystal according to the above (9) or (10) as an active ingredient;

(13-1) a therapeutic agent for hypertension, containing the crystal according to the above (9) or (10) as an active ingredient;

(14) a prophylactic or therapeutic agent for diabetic nephropathy, containing the crystal according to the above (9) or (10) as an active ingredient;

(14-1) a therapeutic agent for diabetic nephropathy, containing the crystal according to the above (9) or (10) as an active ingredient;

(15) use of the crystal according to any one of the above (9) or (10) for producing a medicament;

(16) use of the crystal according to the above (9) or (10) for producing a medicament for preventing or treating hypertension, angina pectoris, acute coronary syndrome, congestive heart failure, nephropathy, arteriosclerosis, cerebral infarction, fibrosis, primary aldosteronism, or a heart disease;

(17) use of the crystal according to the above (9) or (10) for producing a medicament for treating hypertension; and

(18) use of the crystal according to the above (9) or (10) for producing a medicament for treating diabetic nephropathy.

(S)-1-(2-Hydroxyethyl)-4-methyl-N-[4-(methylsulfonyl)phenyl]-5-[2-(trifluoromethyl)phenyl]-1H-pyrrole-3-carboxamide represented by the following formula (A):

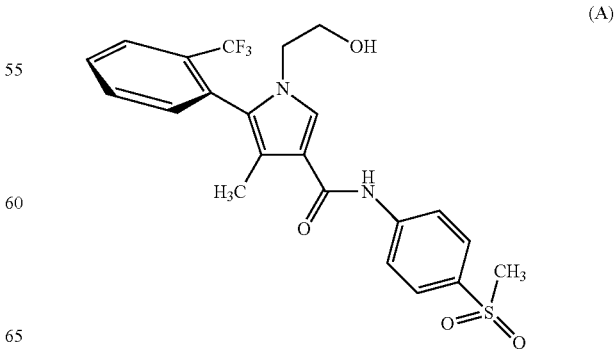

is sometimes referred to as Compound (A) in this description.

In the present invention, "crystal" refers to a solid whose internal structure is three-dimensionally composed of a regular repetition of constituent atoms (or a group thereof), and is distinguished from an amorphous solid which does not have such a regular internal structure.

The crystal of the present invention may sometimes form a hydrate by allowing the crystal to stand in the air to absorb water, thereby having attached water, or by heating the crystal to 25 to 150° C. in usual atmospheric conditions, etc. Further, the crystal of the present invention may sometimes contain a solvent used at the time of crystallization in an attached residual solvent or a solvate.

In this description, the crystal of the present invention is sometimes represented on the basis of powder X-ray diffraction data. In the powder X-ray diffraction, measurement and analysis may be performed by a method conventionally used in this field, and for example, the powder X-ray diffraction can be performed by a method described in the Examples. Further, in general, in the case of a hydrated or dehydrated crystal, the lattice constant thereof is changed by the addition or removal of water of crystallization, and therefore the diffraction angle (2θ) in powder X-ray diffraction may sometimes be changed. Further, the peak intensity may sometimes be changed due to a difference in a crystal growth surface or the like (crystal habit), etc. Therefore, when the crystal of the present invention is represented on the basis of powder X-ray diffraction data, a crystal having identical peak diffraction angles and X-ray diffraction pattern in powder X-ray diffraction, and also hydrated and dehydrated crystals obtained from the crystal are also encompassed within the scope of the present invention.

One preferred embodiment of the crystal of the present invention is a crystal of a pyrrole derivative compound (A). The crystal of Compound (A) has the X-ray diffraction pattern shown in FIG. 1 in a powder X-ray diffraction pattern obtained by irradiation with copper Kα radiation (wavelength λ=1.54 Å). Further, the crystal of Compound (A) has characteristic peaks at diffraction angles 2θ of 6.80, 17.06, 19.24, 22.80, and 25.48 in a powder X-ray diffraction pattern obtained by irradiation with copper Kα radiation (wavelength λ=1.54 Å). Here, "characteristic peak" refers to a peak having a relative intensity of 50 or more when the maximum peak intensity in the powder X-ray diffraction pattern is taken as 100. Further, the crystal of Compound (A) of the present invention is also a crystal which shows main peaks at diffraction angles 2θ of 6.80, 12.32, 13.60, 14.46, 16.30, 17.06, 18.42, 19.24, 19.86, 20.36, 20.82, 21.84, 22.50, 22.80, 23.20, 23.50, 24.60, 24.88, 25.48, 26.96, 27.52, 29.26, 31.80, 32.08, 35.82, 40.32, and 41.36 in a powder X-ray diffraction pattern obtained by irradiation with copper Kα radiation (wavelength λ=1.54 Å). Here, "main peak" refers to a peak having a relative intensity of 15 or more when the maximum peak intensity in the powder X-ray diffraction pattern is taken as 100.

In the present invention, examples of the "C1-C3 alkoxy group" include methoxy, ethoxy, propoxy, and isopropoxy groups. Preferred examples thereof for $R^2$ include a methoxy group.

$R^2$ is preferably a hydrogen atom or a C1-C4 alkoxy group, more preferably a hydrogen atom or a methoxy group, and particularly preferably a hydrogen atom.

n is preferably 2.

A compound represented by the following formula (I):

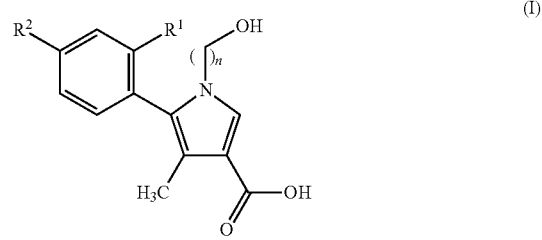

(I)

[wherein $R^1$ represents a methyl group or a trifluoromethyl group, $R^2$ represents a hydrogen atom or a C1-C3 alkoxy group, and n represents an integer selected from 1 to 3] is preferably (RS)-1-(2-hydroxyethyl)-4-methyl-5-[2-(trifluoromethyl)phenyl]-1H-pyrrole-3-carboxic acid represented by the following formula (Ia):

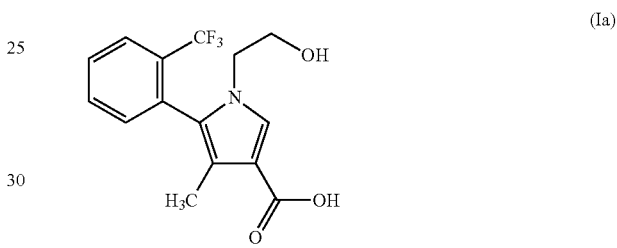

(Ia)

or (RS)-1-(2-hydroxyethyl)-4-methyl-5-[4-methoxy-2-(trifluoromethyl)phenyl]-1H-pyrrole-3-carboxic acid, and more preferably (RS)-1-(2-hydroxyethyl)-4-methyl-5-[2-(trifluoromethyl)phenyl]-1H-pyrrole-3-carboxic acid.

A method for producing a pyrrole derivative compound (A') using the production intermediate compound of the present invention will be described in detail below.

The pyrrole derivative compound (A') can be produced by using a known compound as a starting material and using the following production method of the present invention and intermediates. Incidentally, in the following description, $R^1$, $R^2$, and n represent the same meanings as described above, respectively.

Step A: Production of Intermediate Compound (I)

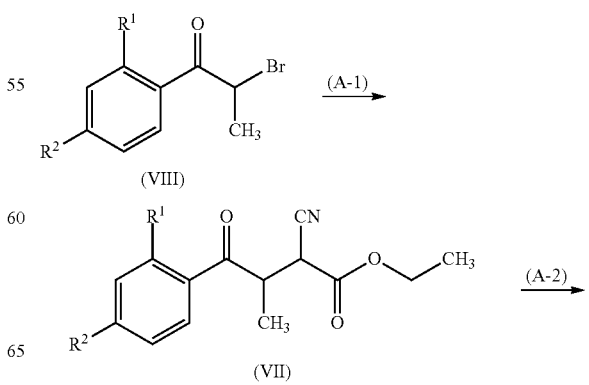

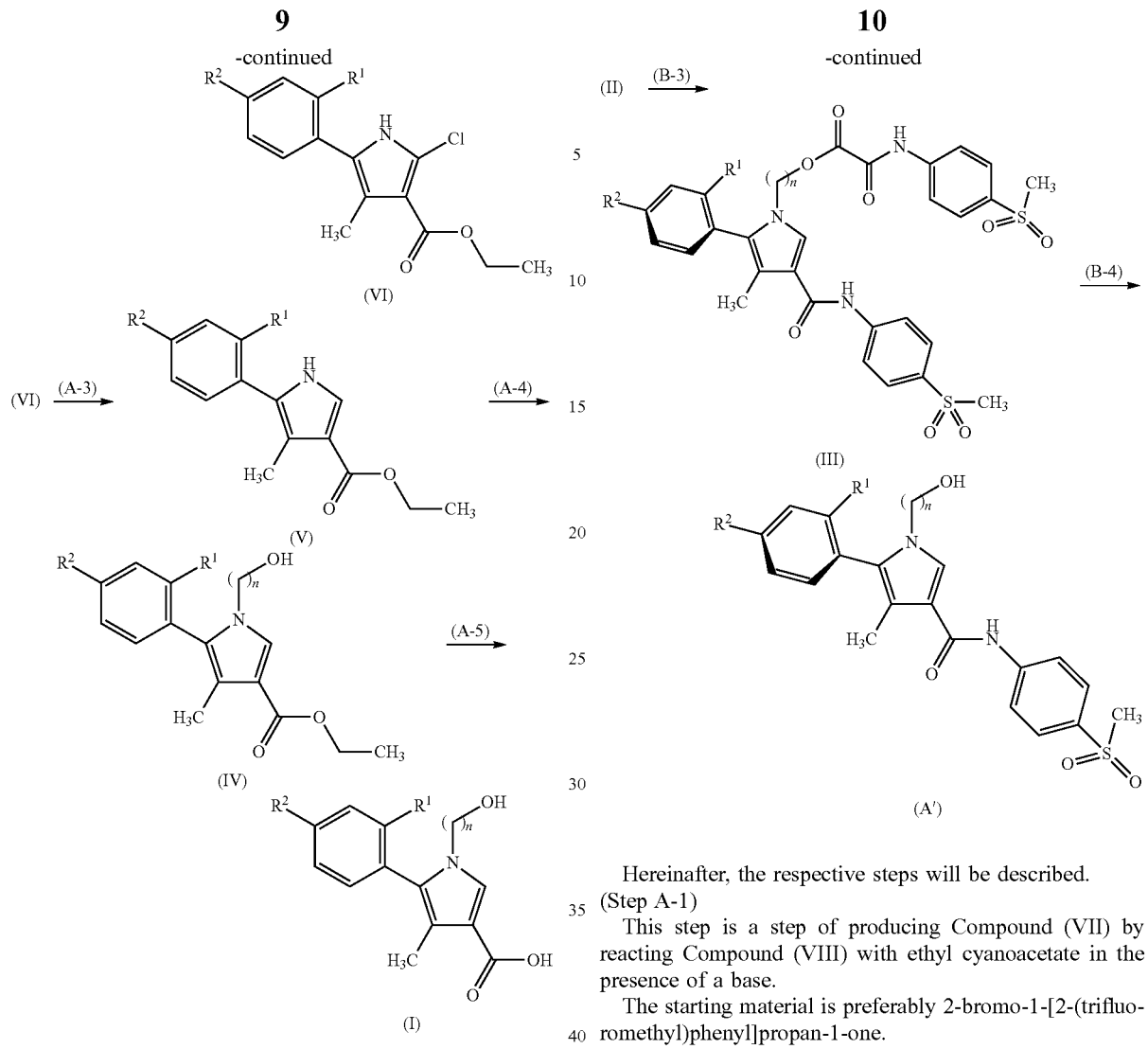

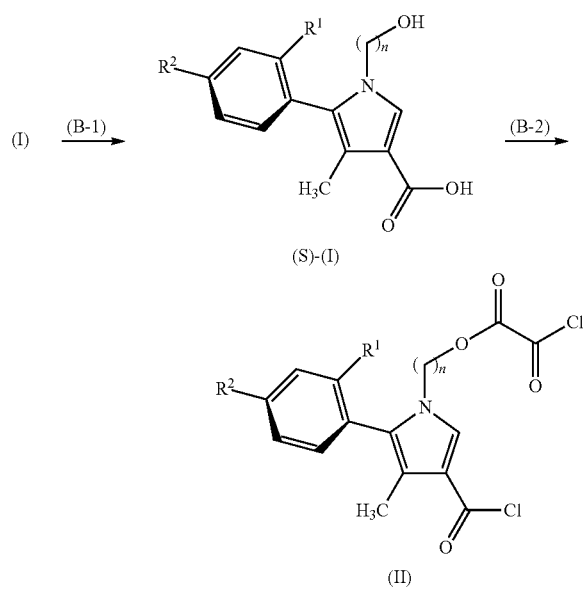

Step B: Production of Pyrrole Derivative Compound (A′)

Hereinafter, the respective steps will be described.

(Step A-1)

This step is a step of producing Compound (VII) by reacting Compound (VIII) with ethyl cyanoacetate in the presence of a base.

The starting material is preferably 2-bromo-1-[2-(trifluoromethyl)phenyl]propan-1-one.

As a solvent, an organic solvent which does not inhibit the reaction and dissolves the starting material to some extent is used. The solvent is preferably an amide, more preferably N,N-dimethylacetamide.

The base is preferably a metal hydride such as sodium hydride or an alkali metal carbonate such as potassium carbonate, more preferably potassium carbonate.

The reaction temperature is from 0° C. to 100° C., preferably from 40° C. to 60° C.

The reaction time is from 0.5 to 12 hours, preferably 1 to 3 hours.

(Step A-2)

This step is a step of producing Compound (VI) by cyclizing Compound (VII) to form a pyrrole ring.

As a solvent, an organic solvent which does not inhibit the reaction and dissolves the starting material to some extent is used. The solvent is preferably an ether such as tetrahydrofuran, an aromatic hydrocarbon such as toluene, or an ester such as ethyl acetate, more preferably ethyl acetate or tetrahydrofuran, particularly preferably ethyl acetate.

As a reagent, it is preferred to blow hydrogen chloride gas in the presence of thionyl chloride, and further concentrated sulfuric acid may be added.

The reaction temperature is from 0° C. to 40° C., preferably room temperature.

The reaction time is from 1 to 30 hours, preferably 10 to 20 hours.

(Step A-3)

This step is a step of producing Compound (V) by removing a chlorine group of Compound (VI).

As a solvent, a mixed solvent of water and an organic solvent which does not inhibit the reaction and dissolves the starting material to some extent is used. The solvent is preferably a mixed solvent of ethanol, tetrahydrofuran, and water.

As a reagent, sodium formate and a 5% palladium-carbon catalyst are preferred.

The reaction temperature is from 0° C. to 100° C., preferably from 40° C. to 60° C.

The reaction time is from 0.5 to 12 hours, preferably 0.5 to 2 hours.

(Step A-4)

This step is a step of producing Compound (IV) by introducing a hydroxy C1-3 alkyl group on the nitrogen atom of the pyrrole group of Compound (V) in a solvent in the presence of a base.

As the solvent, an organic solvent which does not inhibit the reaction and dissolves the starting material to some extent is used. The solvent is preferably an amide such as N,N-dimethylacetamide.

The base is preferably a metal alkoxide such as t-butoxy potassium or t-butoxy sodium or an organic base such as 4-dimethylaminopyridine, more preferably 4-dimethylaminopyridine.

The reagent for introducing a hydroxyalkyl group is preferably 2-iodoethanol, 2-bromoethanol, or ethylene carbonate, more preferably ethylene carbonate.

The reaction temperature is from room temperature to 150° C., preferably from 100° C. to 120° C.

The reaction time is from 1 to 20 hours, preferably 5 to 15 hours.

(Step A-5)

This step is a step of obtaining Compound (I) by alkaline hydrolysis of an ester of Compound (IV).

This step is usually performed in a solvent. The solvent is preferably a mixed solvent of water and an alcohol such as ethanol.

The reagent is not particularly limited as long as it is a basic reagent which hydrolyzes a carboxylate ester, but is preferably sodium hydroxide.

The reaction temperature is from room temperature to 100° C., preferably from 50° C. to 80° C.

The reaction time is from 1 to 20 hours, preferably 5 to 10 hours.

In one embodiment, Compound (Ia), (RS)-1-(2-hydroxyethyl)-4-methyl-5-[2-(trifluoromethyl)phenyl]-1H-pyrrole-3-carboxylic acid, is prepared from ethyl 2-chloro-4-methyl-5-[2-(trifluoromethyl)phenyl]-1H-pyrrole-3-carboxylate (see Example 3) in three steps, as described in Examples 13-15.

Briefly, ethyl 2-chloro-4-methyl-5-[2-(trifluoromethyl)phenyl]-1H-pyrrole-3-carboxylate is treated with ethylene carbonate under standard N-alkylating conditions (e.g., suitable base and solvent) to provide ethyl (RS)-2-chloro-1-(2-hydroxyethyl)-4-methyl-5-[2-(trifluoromethyl)phenyl]-1H-pyrrole-3-carboxylate (see Example 13).

In the second step, ethyl (RS)-2-chloro-1-(2-hydroxyethyl)-4-methyl-5-[2-(trifluoromethyl)phenyl]-1H-pyrrole-3-carboxylate is dechlorinated using a suitable reagent (e.g., 5% palladium-carbon catalyst) under suitable dechlorination conditions (e.g., water, ethanol, sodium formate) to provide ethyl (RS)-1-(2-hydroxyethyl) 4-methyl-5-[2-(trifluoromethyl)phenyl]-1H-pyrrole-3-carboxylate (See Example 14).

In the third step, ethyl (RS)-1-(2-hydroxyethyl)-4-methyl-5-[2-(trifluoromethyl)phenyl]-1H-pyrrole-3-carboxylate is converted to (RS)-1-(2-hydroxyethyl)-4-methyl-5-[2-(trifluoromethyl)phenyl]-1H-pyrrole-3-carboxylic acid, the corresponding acid, by hydrolysis under standard ester hydrolysis conditions (e.g., aqueous sodium hydroxide) followed by isolation of the acid by treatment with a suitable acid (e.g., concentrated hydrochloric acid)(see Example 15).

The preparation of Compound (Ia), as described above, is illustrated schematically below.

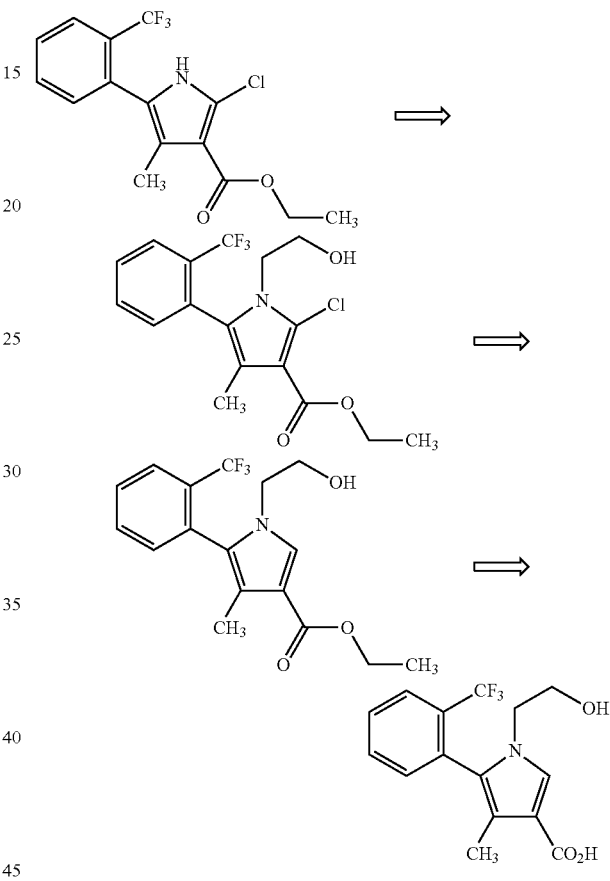

(Step B-1)

This step is a step of producing Compound (s)-(I) by optical resolution of the atropisomer through stirring of the intermediate compound (I) of the present invention and an optically active amine in a solvent, and can be achieved by stirring the above Compound (I) and an optically active amine having a cinchonine skeletal formula in a solvent. A diastereomeric excess can be determined according to a conventional method.

This method is usually performed in a solvent. The solvent is preferably an acetate ester, an amide, or a mixed solvent of water and a solvent selected therefrom, more preferably a mixed solvent of N,N-dimethylacetamide, ethyl acetate, and water. According to need, Compound (I) and the optically active amine are dissolved separately, and to the solution of Compound (I), the solution of the optically active amine may be added dropwise.

In this method, the optically active amine having a cinchonine skeletal formula is preferably one compound selected from cinchonine, quinine, cinchonidine, and quinidine represented by the following group of compounds:

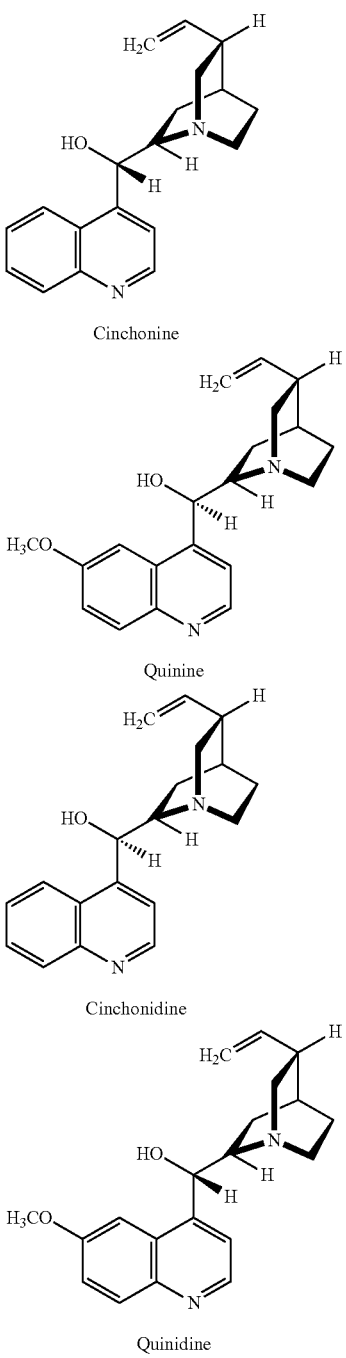

Cinchonine

Quinine

Cinchonidine

Quinidine and more preferably quinine represented by the following formula.

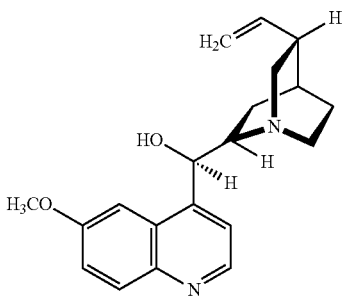

In this method, the amount of the optically active amine having a cinchonine skeletal formula used is preferably from 0.5 to 1 equivalent with respect to Compound (I), more preferably 0.5 equivalents with respect to Compound (I).

In this method, the reaction mixture may be heated or cooled as needed. A method in which the reaction solution is stirred while heating, followed by cooling to generate crystals is preferred. The heating temperature is preferably from room temperature to 100° C., more preferably from 60° C. to 70° C. The cooling temperature is preferably from 20° C. to 30° C.

An amine salt of Compound (s)-(I) obtained by this step can also be converted into the free form using an acid. The acid to be used at this time is not particularly limited as long as it is an acid (an inorganic acid such as hydrochloric acid) usually used for removing an amine salt.

(Step B-2)

This step is a step of obtaining Compound (II) by reacting Compound (s)-(I) and oxalyl chloride in the presence of a base. It is also possible to perform Step B-3 successively without isolating and purifying Compound (II).

This method is usually performed in a solvent. The solvent is preferably an acetate ester, an ether, or a mixed solvent of these solvents, more preferably a mixed solvent of 1,2-dimethoxyethane, ethyl acetate, and tetrahydrofuran.

The base is preferably an organic base such as pyridine.

The reaction temperature is from 0° C. to 20° C., preferably from 0° C. to 10° C.

The reaction time is from 1 to 20 hours, preferably 1 to 10 hours.

(Step B-3)

This step is a step of obtaining Compound (III) by reacting Compound (II) and 4-(methylsulfonyl)aniline in the presence of a base.

This method is usually performed in a solvent. The solvent is preferably a nitrile, more preferably a mixed solvent of acetonitrile and water.

The base is preferably an organic base such as pyridine.

The reaction temperature is from 0° C. to 20° C., preferably from 0° C. to 15° C.

The reaction time is from 1 to 2 hours, preferably 1 hour.

It is also possible to perform Step B-4 successively without isolating and purifying Compound (III), however, a step including a method of isolating Compound (III) is preferred.

(Step B-4)

This step is a step of obtaining the pyrrole derivative compound (A') by converting the hydroxy group of Compound (III) into the free form in the presence of a base.

This method is usually performed in a solvent. The solvent is preferably an acetate ester, a nitrile, an ether, or a mixed solvent of water and a solvent selected therefrom, more preferably a mixed solvent of t-butyl methyl ether, acetonitrile, and water.

The base is preferably a metal hydroxide such as potassium hydroxide.

The reaction temperature is from 0° C. to 100° C., preferably from 10° C. to 30° C.

The reaction time is from 0.5 to 20 hours, preferably from 0.5 to 2 hours.

After completion of the reaction of the above-mentioned respective steps, the target compound can be collected from the reaction mixture according to a conventional method. For example, the reaction mixture is appropriately neutralized, or in the case where insoluble matter is present, after the matter is removed by filtration, an organic solvent immiscible with water such as ethyl acetate is added thereto, followed by washing with water or the like. Thereafter, the organic layer containing the target compound is separated and dried over anhydrous magnesium sulfate or the like, and then, the solvent is distilled off, whereby the target compound can be obtained.

If necessary, the thus obtained target material can be separated and purified by a conventional method, for example, by appropriately combining recrystallization, reprecipitation, or a method conventionally used for separation and purification of an organic compound, for example, a method using a synthetic adsorber such as adsorption column chromatography or partition column chromatography, a method using ion exchange chromatography, or normal-phase or reverse-phase column chromatography using silica gel or alkylated silica gel, and performing elution with a suitable eluent.

According to the above-mentioned steps, (−)-1-(2-hydroxyethyl)-5-[4-methoxy-2-(trifluoromethyl)phenyl]-4-methyl-N-[4-(methylsulfonyl)phenyl]-1H-pyrrole-3-carboxamide described in WO 2008/126831 can be produced.

Another embodiment of the present invention relates to a medicament containing the crystal of the present invention as an active ingredient and a pharmaceutical composition containing the crystal of the present invention.

The medicament containing the crystal of the invention of this application as an active ingredient is preferably provided in the form of a pharmaceutical composition containing the crystal of the present invention and one or more pharmaceutically acceptable carriers. The administration form of the medicament of the present invention is not particularly limited, and the medicament can be administered orally or parenterally, but is preferably administered orally.

The pharmaceutical composition of the present invention contains the crystal of the present invention as Compound (A) at least partially. In the pharmaceutical composition, a crystal form other than the crystal of the invention of this application may exist as Compound (A). The ratio of the crystal of the invention of this application to be contained in the pharmaceutical composition with respect to the total amount of Compound (A) in the pharmaceutical composition may be in the range of 0.01% by weight to 99.9% by weight, for example, 0.01% by weight or more, 0.05% by weight or more, 0.1% by weight or more, 0.5% by weight or more, 1% by weight or more, 2% by weight or more, 3% by weight or more, 4% by weight or more, 5% by weight or more, 10% by weight or more, 20% by weight or more, 30% by weight or more, 40% by weight or more, 50% by weight or more, 60% by weight or more, 70% by weight or more, 80% by weight or more, 90% by weight or more, 95% by weight or more, 96% by weight or more, 97% by weight or more, 98% by weight or more, 99% by weight or more, 99.5% by weight or more, 99.6% by weight or more, 99.7% by weight or more, 99.8% by weight or more, or 99.9% by weight or more. Whether or not the crystal of the invention of this application is contained in the pharmaceutical composition can be confirmed by an instrumental analysis method (for example, powder X-ray diffraction, thermal analysis, infrared absorption spectrum, etc.) described in this description.

The pharmaceutical composition of the present invention contains the crystal of the present invention and a pharmaceutically acceptable carrier, and can be administered in the form of any of various injections through intravenous injection, intramuscular injection, subcutaneous injection, or the like, or through any of various methods such as oral administration or transdermal administration. A pharmaceutically acceptable carrier refers to a pharmaceutically acceptable material (for example, an excipient, a diluent, an additive, a solvent, etc.) which is involved in transport of the crystal of the present invention from a given body part or organ to another body part or organ.

As a method for preparing a formulation, for example, an appropriate formulation (for example, an oral preparation or an injection) is selected according to the administration method, and can be prepared by a conventionally used preparation method for various formulations. Examples of oral preparations can include a tablet, a powder, a granule, a capsule, a pill, a troche, a solution, a syrup, an elixir, an emulsion, and an oily or aqueous suspension. In the case of an injection, a stabilizer, a preservative, a solubilizing agent, or the like can also be used in the formulation. It is also possible to form a solid preparation as a formulation to be prepared before use by placing a solution which may contain such a pharmaceutical aid or the like in a container, followed by lyophilization or the like. In addition, a single dosage may be packed in one container, or multiple dosages may be packed in one container.

Examples of solid preparations include a tablet, a powder, a granule, a capsule, a pill, and a troche. These solid preparations may contain a pharmaceutically acceptable additive along with the crystal of the present invention. Examples of additives include a filler, an expander, a binder, a disintegrant, a solubilization enhancer, a wetting agent, and a lubricant, and the solid preparation can be prepared by selecting an additive therefrom according to need and mixing.

Examples of liquid preparations include a solution, a syrup, an elixir, an emulsion, and a suspension. These liquid preparations may contain a pharmaceutically acceptable additive along with the crystal of the present invention. Examples of additives include a suspending agent and an emulsifying agent, and the liquid preparation can be prepared by selecting an additive therefrom according to need and mixing.

For example, in the case of a tablet, in the entire pharmaceutical composition, the content of a binder is generally from 1 to 10 parts by weight (preferably from 2 to 5 parts by weight), the content of a disintegrant is generally from 1 to 40 parts by weight (preferably from 5 to 30 parts by weight), the content of a lubricant is generally from 0.1 to 10 parts by weight (preferably from 0.5 to 3 parts by weight), and the content of a fluidizing agent is generally from 0.1 to 10 parts by weight (preferably from 0.5 to 5 parts by weight).

The pharmaceutical composition of the present invention can be administered to a warm-blooded animal (particularly a human being). The dose of Compound (A) or a pharmacologically acceptable salt thereof which is an active ingredient varies depending on the various conditions such as symptoms, age, and body weight of a patient, however, in the case of, for example, oral administration, it can be administered to a human being at a dose of 0.1 mg/body to 20 mg/body (preferably 0.5 mg/body to 10 mg/body) one to three times per day depending on the symptoms.

Advantageous Effects of Invention

According to the present invention, a method for producing a pyrrole derivative compound (A') having mineralocorticoid receptor antagonistic activity and a production intermediate compound thereof are provided. Further, a crystal of (S)-1-(2-hydroxyethyl)-4-methyl-N-[4-(methylsulfonyl)phenyl]-5-[2-(trifluoromethyl)phenyl]-1H-pyrrole-3-carboxamide, a method for producing the same, and a production intermediate compound thereof are provided. The crystal of the present invention has excellent stability and is useful as a medicament such as an antihypertensive drug.

BRIEF DESCRIPTION OF DRAWINGS

FIG. 2 shows a DSC curve of a crystal (Crystal A) obtained in Example 8. In the drawing, the ordinate represents heat flow (mW), and the abscissa represents temperature (° C.).

DESCRIPTION OF EMBODIMENTS

Figure 1:
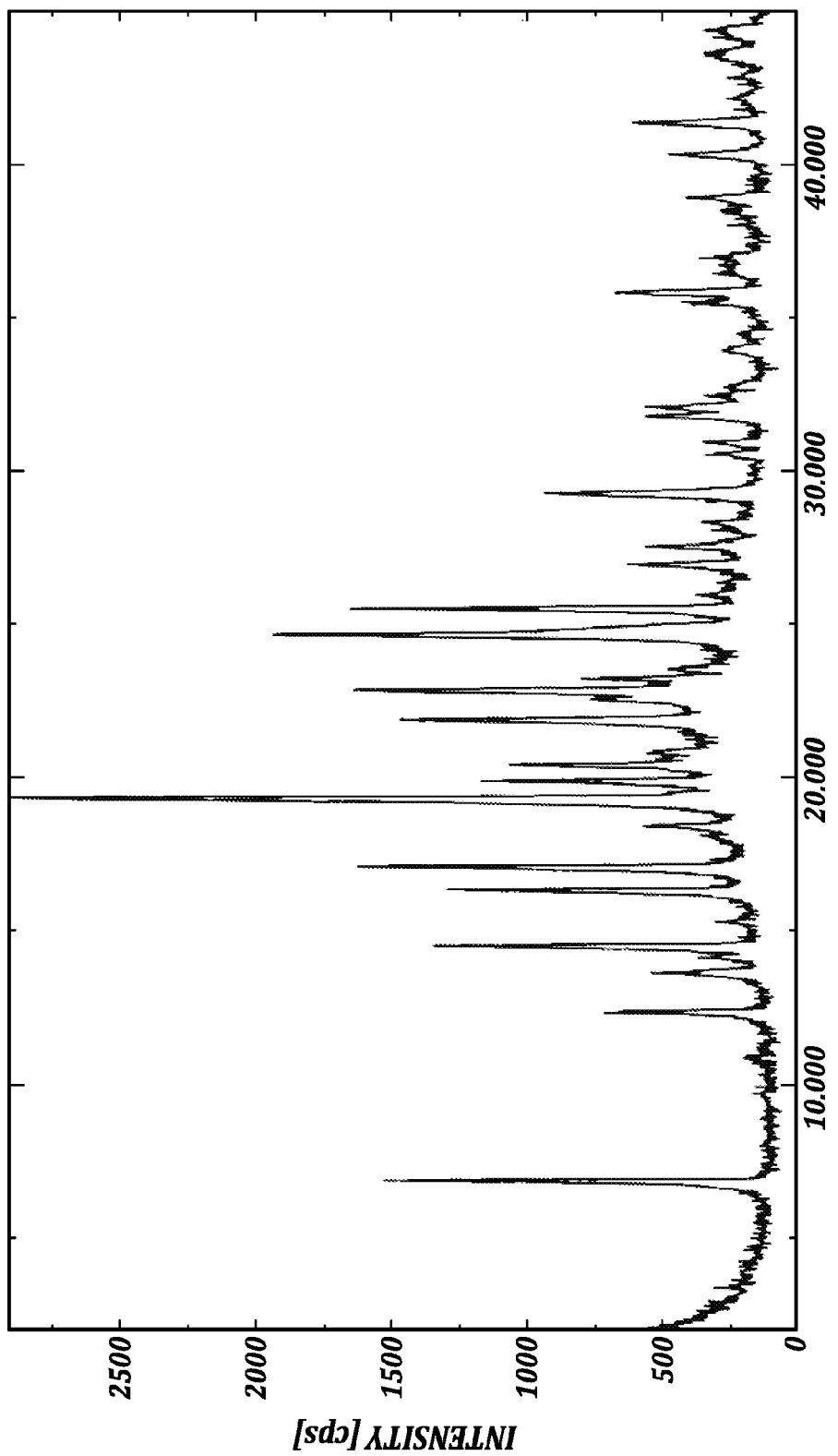
FIG. 1 shows a powder X-ray diffraction pattern of the crystal obtained in Example 8. In the drawing, the ordinate represents diffraction intensity in units of count/sec (cps), and the abscissa represents values of diffraction angle 2θ.

Hereinafter, the present invention will be described in more detail by showing Examples of the present invention and the like, however, the scope of the present invention is not limited thereto.

EXAMPLES

Example 1

2-Bromo-1-[2-(trifluoromethyl)phenyl]propan-1-one

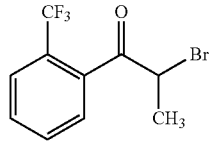

To 1-[2-(trifluoromethyl)phenyl]propan-1-one (75 g (370 mmol)), t-butyl methyl ether (750 mL) and bromine (1.18 g (7.4 mmol)) were added. The resulting mixture was stirred at 15 to 30° C. for about 30 minutes, and after it was confirmed that the color of bromine disappeared, the mixture was cooled to 0 to 5° C. While maintaining the temperature at 0 to 10° C., bromine (59.13 g (370 mmol)) was added thereto, and the resulting mixture was stirred. After the mixture was stirred for about 2.5 hours, a 10 w/v % aqueous potassium carbonate solution (300 mL) was added thereto while maintaining the temperature at 0 to 25° C., and sodium sulfite (7.5 g) was further added thereto, followed by heating to 20 to 30° C. This solution was subjected to liquid separation, and to the obtained organic layer, water (225 mL) was added to wash the organic layer. Thereafter, the organic layer was concentrated under reduced pressure, whereby a t-butyl methyl ether solution (225 mL) of the title compound was obtained.

$^1$H NMR (400 MHz, CDCl$_3$) δ: 1.91 (3H, d, J=4.0 Hz), 4.97 (1H, q, J=6.7 Hz), 7.60-7.74 (4H, m)

Example 2

Ethyl 2-cyano-3-methyl-4-oxo-4-[2-(trifluoromethyl)phenyl]butanoate

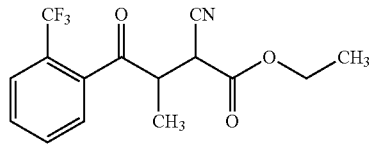 [SMILES: CCOC(=O)C(C#N)C(C)C(=O)c1ccccc1C(F)(F)F]

To the 2-bromo-1-[2-(trifluoromethyl)phenyl]propan-1-one/t-butyl methyl ether solution (220 mL) obtained in Example 1, dimethylacetamide (367 mL), cyanoethyl acetate (53.39 g (472 mmol)), and potassium carbonate (60.26 g (436 mmol)) were sequentially added, and the resulting mixture was heated to 45 to 55° C. and stirred. After the mixture was stirred for about 2 hours, the mixture was cooled to 20 to 30° C., and then water (734 mL) and toluene (367 mL) were added thereto to effect extraction. Then, water (513 mL) was added to the resulting organic layer to wash the organic layer (washing was performed twice). Thereafter, the obtained organic layer was concentrated under reduced pressure, whereby a toluene solution (220 mL) of the title compound was obtained.

$^1$H NMR (400 MHz, CDCl$_3$) δ: 1.33-1.38 (6H, m), 3.80-3.93 (2H, m), 4.28-4.33 (2H, m), 7.58-7.79 (4H, m).

Example 3

Ethyl 2-chloro-4-methyl-5-[2-(trifluoromethyl)phenyl]-1H-pyrrole-3-carboxylate

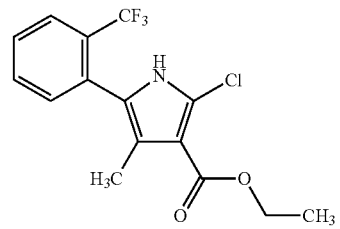 [SMILES: CCOC(=O)c1c(Cl)[nH]c(-c2ccccc2C(F)(F)F)c1C]

To the toluene solution (217 mL) of ethyl 2-cyano-3-methyl-4-oxo-4-[2-(trifluoromethyl)phenyl]butanoate obtained by the production method of Example 2, ethyl acetate (362 mL) and thionyl chloride (42.59 g (358 mmol)) were added at 20 to 30° C., followed by cooling to −10 to 5° C. Then, hydrogen chloride gas (52.21 g (1432 mmol)) was blown into the mixture, and concentrated sulfuric acid (17.83 g (179 mmol)) was further added thereto, and the resulting mixture was heated and stirred at 15 to 30° C. After the mixture was stirred for about 20 hours, ethyl acetate (1086 mL) was added thereto, followed by heating to 30 to 40° C., and water (362 mL) was added thereto, and then, the resulting mixture was subjected to liquid separation. To the organic layer obtained by liquid separation, water (362 mL) was added, followed by liquid separation, and then, a 5 w/v % aqueous sodium hydrogen carbonate solution (362 mL) was added thereto, followed by liquid separation.

Subsequently, the organic layer was concentrated under reduced pressure, and toluene (579 mL) was further added thereto, followed by concentration under reduced pressure, and then, toluene (72 mL) was added thereto, and the mixture was cooled to 0 to 5° C. After the mixture was stirred for about 2 hours, the deposited crystal was filtered and washed with toluene (217 mL) cooled to 0 to 5° C. The obtained wet crystal product was dried under reduced pressure at 40° C., whereby the title compound was obtained (97.55 g, yield: 82.1%).

$^1$H NMR (400 MHz, CDCl$_3$) δ: 1.38 (3H, t, J=7.1 Hz), 2.11 (3H, s), 4.32 (2H, q, J=7.1 Hz), 7.39 (1H, d, J=7.3 Hz), 7.50-7.62 (2H, m), 7.77 (1H, d, J=8.0 Hz), 8.31 (1H, br).

Example 4

Ethyl 4-methyl-5-[2-(trifluoromethyl)phenyl]-1H-pyrrole-3-carboxylate

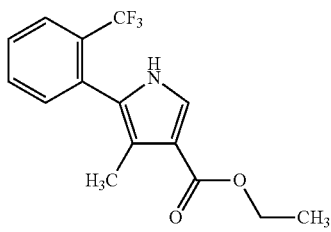 [SMILES: CCOC(=O)c1c[nH]c(-c2ccccc2C(F)(F)F)c1C]

To ethyl 2-chloro-4-methyl-5-[2-(trifluoromethyl)phenyl]-1H-pyrrole-3-carboxylate (97.32 g (293 mmol)) obtained by the production method of Example 3, ethanol (662 mL), tetrahydrofuran (117 mL), water (49 mL), sodium formate (25.91 g (381 mmol)), and a 5% palladium-carbon catalyst (water content: 52.1%, 10.16 g) were added at room temperature, and the resulting mixture was heated to 55 to 65° C. and stirred. After the mixture was stirred for about 1 hour, the mixture was cooled to 40° C. or lower, and tetrahydrofuran (97 mL) and a filter aid (KC Flock, Nippon Paper Industries) (4.87 g) were added thereto. Then, the catalyst was filtered, and the residue was washed with ethanol (389 mL). The filtrate and the ethanol solution used for washing were combined, and the combined solution was concentrated under reduced pressure. Thereafter, water (778 mL) was added thereto and the mixture was stirred at 20 to 30° C. for 0.5 hours or more. The deposited crystal was filtered and washed with a mixed solution of ethanol/water=7/8 (292 mL). The thus obtained wet crystal product was dried under reduced pressure at 40° C., whereby the title compound was obtained (86.23 g, yield: 98.9%).

$^1$H NMR (400 MHz, CDCl$_3$) δ: 1.35 (3H, t, J=7.1 Hz), 2.18 (3H, s), 4.29 (2H, m), 7.40-7.61 (4H, m), 7.77 (1H, d, J=7.9 Hz), 8.39 (1H, br)

Example 5

Ethyl (RS)-1-(2-hydroxyethyl)-4-methyl-5-[2-(trifluoromethyl)phenyl]-1H-pyrrole-3-carboxylate

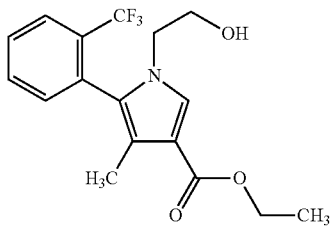 [SMILES: CCOC(=O)c1cn(CCO)c(-c2ccccc2C(F)(F)F)c1C]

To ethyl 4-methyl-5-[2-(trifluoromethyl)phenyl]-1H-pyrrole-3-carboxylate (65.15 g (219 mmol)) obtained by the production method of Example 4, N,N-dimethylacetamide (261 mL), ethylene carbonate (28.95 g (328.7 mmol)), and 4-dimethylaminopyridine (2.68 g (21.9 mmol)) were sequentially added at room temperature, and the resulting mixture was heated to 105 to 120° C. and stirred. After the mixture was stirred for about 10 hours, the mixture was cooled to 20 to 30° C., and toluene (1303 mL) and water (326 mL) were added thereto, and the organic layer was extracted. Then, water (326 mL) was added to the organic layer to wash the organic layer (washing was performed three times). The obtained organic layer was concentrated under reduced pressure, and ethanol (652 mL) was added thereto, and the resulting mixture was further concentrated under reduced pressure. Thereafter, ethanol (130 mL) was added thereto, whereby an ethanol solution of the title compound (326 mL) was obtained.

$^1$H NMR (400 MHz, CDCl$_3$) δ: 1.35 (3H, t, J=7.1 Hz), 1.84 (1H, broad singlet), 2.00 (3H, s), 3.63-3.77 (4H, m), 4.27 (2H, m), 7.35-7.79 (5H, m)

Example 6

(RS)-1-(2-Hydroxyethyl)-4-methyl-5-[2-(trifluoromethyl)phenyl]-1H-pyrrole-3-carboxylic acid

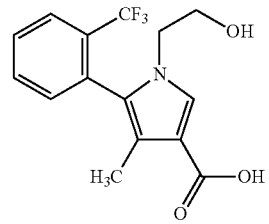 [SMILES: Cc1c(C(=O)O)cn(CCO)c1-c1ccccc1C(F)(F)F]

To the solution of ethyl (RS)-1-(2-hydroxyethyl)-4-methyl-5-[2-(trifluoromethyl)phenyl]-1H-pyrrole-3-carboxylate/ethanol solution (321 mL) obtained by the production method of Example 5, water (128.6 mL) and sodium hydroxide (21.4 g (519 mmol)) were added at room temperature, and the resulting mixture was heated and stirred at 65 to 78° C. After the mixture was stirred for about 6 hours, the mixture was cooled to 20 to 30° C., and water (193 mL) was added thereto. Then, the pH of the resulting mixture was adjusted to 5.5 to 6.5 using 6 N hydrochloric acid while maintaining the temperature at 20 to 30° C. To the mixture whose pH was adjusted, (RS)-1-(2-hydroxyethyl)-4-methyl-5-[2-(trifluoromethyl)phenyl]-1H-pyrrole-3-carboxylic acid (6.4 mg) was added as a seed crystal, and water (193 mL) was further added. Then, the mixture was cooled to 0 to 5° C., and again, the pH of the mixture was adjusted to 3 to 4 using concentrated hydrochloric acid, and the mixture was stirred for about 1 hour. Thereafter, the deposited crystal was filtered and washed with a 20% aqueous ethanol solution (93 mL) cooled to 0 to 5° C. The thus obtained wet crystal product was dried under reduced pressure at 40° C., whereby the title compound was obtained (64.32 g, yield: 95.0%).

$^1$H NMR (400 MHz, DMSO-d$_6$) δ: 1.87 (3H, s), 3.38-3.68 (4H, m), 7.43-7.89 (5H, m)

Example 7

(S)-1-(2-Hydroxyethyl)-4-methyl-5-[2-(trifluoromethyl)phenyl]-1H-pyrrole-3-carboxylic acid quinine salt (7-1) (S)-1-(2-Hydroxyethyl)-4-methyl-5-[2-(trifluoromethyl)phenyl]-1H-pyrrole-3-carboxylic acid quinine salt To (RS)-1-(2-hydroxyethyl)-4-methyl-5-[2-(trifluoromethyl)phenyl]-1H-pyrrole-3-carboxylic acid (50.00 g (160 mmol)) obtained by the production method of Example 6, N,N-dimethylacetamide (25 mL) and ethyl acetate (85 mL) were added at room temperature and dissolved therein. (Solution 1)

To quinine (31.05 g (96 mmol)), N,N-dimethylacetamide (25 mL), ethyl acetate (350 mL), and water (15 mL) were added, and the resulting mixture was heated to 65 to 70° C., and then, Solution 1 was added dropwise thereto. After the mixture was stirred at 65 to 70° C. for about 1 hour, the mixture was gradually cooled to 0 to 5° C. (cooling rate as a guide: about 0.3° C./min) and stirred for about 0.5 hours at that temperature. The resulting crystal was filtered and washed with ethyl acetate (100 mL) cooled to 5° C. or lower, and the obtained wet crystal product was dried under reduced pressure at 40° C., whereby the title compound (43.66 g) was obtained (yield: 42.9%). The diastereomeric excess of the obtained salt was 98.3% de.

$^1$H NMR (400 MHz, DMSO-$d_6$) δ: 1.30-2.20 (10H, m), 2.41-2.49 (2H, m), 2.85-3.49 (6H, m), 3.65-3.66 (1H, m), 3.88 (3H, s), 4.82 (1H, broad singlet), 4.92-5.00 (2H, m), 5.23-5.25 (1H, m), 5.60 (1H, br), 5.80-6.00 (1H, m), 7.36-7.92 (9H, m), 8.67 (1H, d, J=4.6 Hz)

(7-2) HPLC determination for diastereomeric excess (% de) of (S)-1-(2-hydroxyethyl)-4-methyl-5-[2-(trifluoromethyl)phenyl]-1H-pyrrole-3-carboxyl is acid quinine salt About 10 mg of the title compound was collected and diluted with a 50 v/v % aqueous acetonitrile solution to 10 mL, whereby a sample solution was prepared.
Column: DAICEL CHIRALPAK IC-3 (4.6 mm I.D.×250 mm, 3 μm)
Mobile phase A: a 0.02 mol/L phosphate buffer solution (pH 3)
Mobile phase B: acetonitrile
Supply of mobile phase: The mixing ratio of the mobile phase A to the mobile phase B is shown in the following Table 1.

TABLE 1

| Time (min) | Mobile phase A (vol %) | Mobile phase B (vol %) |
|---|---|---|
| 0-13 | 100 | 0 |
| 13-18 | 100 → 40 | 0 → 60 |
| 18-20 | 100 | 0 |

Detection: UV 237 nm
Flow rate: about 0.8 mL/min
Column temperature: constant temperature at around 30° C.
Measurement time: about 20 min
Injection volume: 5 μL The diastereomeric excess (% de) was calculated according to the following formula using the peak area ratios of the title compound (retention time: about 12 min) and the R form (retention time: about 13 min).

% de={[(the peak area ratio of the title compound (S form))−(the peak area ratio of the R form)]÷
[(the peak area ratio of the title compound (S form))+(the peak area ratio of the R form)]}×
100

Example 8

(S)-1-(2-Hydroxyethyl)-4-methyl-N-[4-(methylsulfonyl)phenyl]-5-[2-(trifluoromethyl)phenyl]-1H-pyrrole-3-carboxamide (Compound (A))

(8-1) (S)-1-(2-Hydroxyethyl)-4-methyl-5-[2-(trifluoromethyl)phenyl]-1H-pyrrole-3-carboxylic acid To (S)-1-(2-hydroxyethyl)-4-methyl-5-[2-(trifluoromethyl)phenyl]-1H-pyrrole-3-carboxylic acid (8α,9R)-6'-methoxycinchonan-9-ol (40.00 g (63 mmol)) obtained by the production method of Example 7, ethyl acetate (400 mL) and a 2 N aqueous hydrochloric acid solution (100 mL) were added, and the resulting mixture was stirred at room temperature, followed by liquid separation. The obtained organic layer was concentrated under reduced pressure (120 mL), ethyl acetate (200 mL) was added thereto, and the resulting mixture was further concentrated under reduced pressure, whereby a solution containing the title compound (120 mL) was obtained.

(8-2) 2-((S)-3-Methyl-4-{[4-(methylsulfonyl)phenyl]carbamoyl}-2-[2-(trifluoromethyl)phenyl]-1H-pyrrol-1-yl)ethyl N-{4-(methylsulfonyl)phenyl]amino}oxamate Ethyl acetate (240 mL), tetrahydrofuran (80 mL), and oxalyl chloride (20.72 g (163 mmol)) were mixed, and the resulting mixture was cooled to 10 to 15° C. Subsequently, the solution obtained in Example (8-1) was added thereto while maintaining the temperature at 10 to 15° C., and the resulting mixture was heated to 15 to 20° C. and stirred for about 1 hour. After stirring, acetonitrile (120 mL) and pyridine (2.46 g (31 mmol)) were added thereto, and the reaction solution was concentrated under reduced pressure (120 mL), and acetonitrile (200 mL) was added thereto, and the resulting mixture was further concentrated under reduced pressure (120 mL).

After completion of concentration under reduced pressure, acetonitrile (200 mL) was added thereto, and the resulting mixture was cooled to 10 to 15° C. (Reaction Solution 1).

After acetonitrile (240 mL), pyridine (12.39 g (157 mmol)), and 4-(methylsulfonyl)aniline (26.85 g (157 mmol)) were sequentially added, Reaction Solution 1 was added thereto while maintaining the temperature at 10 to 15° C., and the resulting mixture was heated to 20 to 25° C. and stirred for about 1 hour.

To the thus obtained reaction solution, acetonitrile (40 mL), a 2 N aqueous hydrochloric acid solution (120 mL), and sodium chloride (10.0 g) were added, and the resulting mixture was stirred, followed by liquid separation. Again, to the organic layer, a 2 N aqueous hydrochloric acid solution (120 mL) and sodium chloride (10.0 g) were added, and the resulting mixture was stirred, followed by liquid separation. The obtained organic layer was filtered and concentrated under reduced pressure (400 mL). To the concentrated liquid, water (360 mL) was added, and stirred for about 1 hour. Then, the resulting crystal was filtered and washed with a 50 v/v % aqueous acetonitrile solution (120 mL), whereby a wet product of the title compound (undried product, 62.02 g) was obtained.

$^1$H NMR (500 MHz, DMSO-$d_6$) δ: 1.94 (s, 3H), 3.19 (s, 3H), 3.20 (s, 3H), 3.81 (t, 1H), 4.12 (t, 1H), 4.45 (t, 2H, J=5.81 Hz), 7.62 (t, 1H, J=4.39 Hz), 7.74 (t, 2H, J=3.68 Hz), 7.86 (dd, 3H), 7.92 (dd, 3H, J=6.94, 2.13 Hz), 7.97 (dd, 2H, J=6.80, 1.98 Hz), 8.02 (dd, 2H), 10.03 (s, 1H), 11.19 (s, 1H)

(8-3) (S)-1-(2-Hydroxyethyl)-4-methyl-N-[4-(methylsulfonyl)phenyl]-5-[2-(trifluoromethyl)phenyl]-1H-pyrrole-3-carboxamide (Compound (A))

To the crystal of the wet product obtained in (8-2), t-butyl methyl ether (200 mL), acetonitrile (40 mL), a 48 w/w aqueous potassium hydroxide solution (16 g), and water (200 mL) were added, and the resulting mixture was stirred at 25 to 35° C. for about 2 hours. After stirring, liquid separation was performed, and the obtained organic layer was concentrated under reduced pressure (120 mL), and ethanol (240 mL) was added thereto, and the resulting mixture was further concentrated under reduced pressure (120 mL). After completion of concentration under reduced pressure, ethanol (36 mL) and water (12 mL) were added thereto, and the resulting mixture was heated to 35 to 45° C., and then, water (280 mL) was added dropwise thereto while maintaining the temperature at 35 to 45° C. to deposit a crystal. The crystallization solution was cooled to room temperature, and the crystal was filtered. Then, the crystal was washed with a 30 v/v % aqueous ethanol solution (80 mL) and dried under reduced pressure at 40° C., whereby the title compound was obtained in the form of a crystal (26.26 g, yield: 89.7%). The amount of enantiomer of the obtained crystal was 0.3%.

$^1$H NMR (400 MHz, CDCl$_3$) δ: 1.74 (1H, broad singlet), 2.08 (3H, s), 3.04 (3H, s), 3.63-3.80 (4H, m), 7.36 (1H, d, J=7.2 Hz), 7.48 (1H, s), 7.58-7.67 (2H, m), 7.77-7.90 (6H, m)

(8-4) HPLC determination method for amount (%) of enantiomer of (S)-1-(2-hydroxyethyl)-4-methyl-N-[4-(methylsulfonyl)phenyl]-5-[2-(trifluoromethyl)phenyl]-1H-pyrrole-3-carboxamide About 10 mg of the title compound was collected and diluted with a 50 v/v % aqueous acetonitrile solution to 10 mL, whereby a sample solution was prepared.
Column: DAICEL CHIRALPAK OJ-RH (4.6 mm I.D.×150 mm, 5 μm)
Mobile phase A: acetonitrile/water=9/16
Mobile phase B: acetonitrile
Supply of mobile phase: The mixing ratio of the mobile phase A to the mobile phase B is shown in the following Table 2.

TABLE 2

| Time (min) | Mobile phase A (vol %) | Mobile phase B (vol %) |
|---|---|---|
| 0-10 | 100 | 0 |
| 10-20 | 100 → 30 | 0 → 70 |
| 20-30 | 100 | 0 |

Detection: UV 287 nm
Flow rate: about 0.8 mL/min
Column temperature: constant temperature at around 30° C.
Measurement time: about 30 min
Injection volume: 5 μL The amount of enantiomer was calculated according to the following formula using the peak areas of the title compound (retention time: about 9.2 min) and the enantiomer (retention time: about 8.2 min).

Amount of enantiomer (%)=(the peak area of the enantiomer÷the peak area of the title compound)×100

(8-5) X-ray diffractometry of (S)-1-(2-hydroxyethyl)-4-methyl-N-[4-(methylsulfonyl)phenyl]-5-[2-(trifluoromethyl)phenyl]-1H-pyrrole-3-carboxamide X-ray diffractometry was performed for the crystal of the title compound obtained in (8-3) by filling the sample in a glass sample holder using an X-ray diffractometer RINT 2200V manufactured by Rigaku Corporation under the following conditions. The diffraction pattern of the powder X-ray diffraction (CuKα, λ=1.54 Å) of the obtained crystal is shown in FIG. 1, and the peaks having a relative intensity of 5 or more when the maximum peak intensity in FIG. 1 was taken as 100 are shown in Table 3.

TABLE 3

| Peak No. | 2θ | d value | Relative intensity |
|---|---|---|---|
| 1 | 6.80 | 12.99 | 52 |
| 2 | 9.90 | 8.93 | 5 |
| 3 | 10.82 | 8.17 | 7 |
| 4 | 11.18 | 7.91 | 5 |
| 5 | 12.32 | 7.18 | 22 |
| 6 | 12.58 | 7.03 | 5 |
| 7 | 13.60 | 6.51 | 18 |
| 8 | 14.10 | 6.28 | 12 |
| 9 | 14.46 | 6.12 | 46 |
| 10 | 14.90 | 5.94 | 6 |
| 11 | 15.28 | 5.798 | 9 |
| 12 | 15.76 | 5.62 | 6 |
| 13 | 16.30 | 5.43 | 44 |
| 14 | 17.06 | 5.19 | 55 |
| 15 | 17.36 | 5.10 | 8 |
| 16 | 17.62 | 5.03 | 8 |
| 17 | 17.82 | 4.97 | 8 |
| 18 | 18.42 | 4.81 | 18 |
| 19 | 19.24 | 4.61 | 100 |
| 20 | 19.86 | 4.47 | 37 |
| 21 | 20.36 | 4.36 | 35 |
| 22 | 20.84 | 4.26 | 18 |
| 23 | 21.84 | 4.07 | 50 |
| 24 | 22.52 | 3.94 | 24 |
| 25 | 22.80 | 3.90 | 56 |
| 26 | 23.20 | 3.83 | 27 |
| 27 | 23.50 | 3.78 | 14 |
| 28 | 24.60 | 3.62 | 66 |
| 29 | 25.48 | 3.499 | 56 |
| 30 | 25.98 | 3.43 | 11 |
| 31 | 26.96 | 3.30 | 21 |
| 32 | 27.52 | 3.24 | 16 |
| 33 | 28.10 | 3.17 | 9 |
| 34 | 28.32 | 3.15 | 12 |
| 35 | 28.66 | 3.11 | 6 |
| 36 | 29.26 | 3.05 | 30 |
| 37 | 30.56 | 2.92 | 10 |
| 38 | 30.94 | 2.89 | 11 |
| 39 | 31.80 | 2.81 | 19 |
| 40 | 32.08 | 2.79 | 17 |
| 41 | 32.46 | 2.76 | 8 |
| 42 | 32.74 | 2.73 | 9 |
| 43 | 33.96 | 2.64 | 9 |
| 44 | 34.54 | 2.59 | 6 |
| 45 | 35.00 | 2.56 | 5 |
| 46 | 35.50 | 2.53 | 14 |
| 47 | 35.82 | 2.50 | 23 |
| 48 | 36.44 | 2.46 | 11 |
| 49 | 36.98 | 2.43 | 10 |
| 50 | 37.44 | 2.40 | 6 |
| 51 | 38.06 | 2.36 | 6 |
| 52 | 38.92 | 2.31 | 12 |
| 53 | 39.54 | 2.28 | 5 |
| 54 | 40.34 | 2.23 | 16 |
| 55 | 40.98 | 2.20 | 5 |
| 56 | 41.36 | 2.18 | 21 |
| 57 | 41.96 | 2.15 | 7 |
| 58 | 42.18 | 2.14 | 9 |
| 59 | 43.64 | 2.07 | 10 |
| 60 | 44.42 | 2.04 | 11 |

<Analysis Conditions>
X ray: Cu-Kα1/40 kV/40 mA
Goniometer: Ultima+horizontal goniometer I
2θ scanning range: 2 to 45°

(8-6) Differential scanning calorimetry of (S)-1-(2-hydroxyethyl)-4-methyl-N-[4-(methylsulfonyl)phenyl]-5-[2-(trifluoromethyl)phenyl]-1H-pyrrole-3-carboxamide About 5 mg of a test compound was weighed and placed on an aluminum pan for measurement, and calorimetry was performed in a temperature range from room temperature to 250° C. at a heating rate of 5° C./min in a state where the pan was opened using a differential scanning calorimeter DSC 3100 manufactured by Mac Science Corporation. The DSC curve obtained by the differential scanning calorimetry is shown in FIG. 2.

Example 9

Production of (S)-1-(2-hydroxyethyl)-4-methyl-5-[2-(trifluoromethyl)phenyl]-1H-pyrrole-3-carboxylic acid by optical resolution of racemic compound (9-1) Effect of Various Amines or Various Solvents Various solvents were added to (RS)-1-(2-hydroxyethyl)-4-methyl-5-[2-(trifluoromethyl)phenyl]-1H-pyrrole-3-carboxylic acid (100 mg (319.2 mmol)) and various amines (0.5 equivalents) at room temperature. The resulting mixture was stirred at room temperature for about 1 hour or stirred for about 1 hour while heating, and thereafter gradually cooled to 20 to 30° C., and then, the mixture was stirred for about 0.5 hours at that temperature. Then, the resulting crystal was filtered, and the obtained wet crystal product was dried under reduced pressure, whereby the crystal was obtained. Further, the diastereomeric excess of the obtained salt was determined.

(9-2) HPLC Determination Method for Diastereomeric Excess of Title Compound

About 10 mg of the title compound was collected and diluted with a mobile phase to 20 mL, whereby a sample solution was prepared.
Column: DAICEL CHIRALCEL OD-RH (4.6 mm I.D.×150 mm, 5 μm)
Mobile phase: a 0.1 v/v % aqueous acetic acid solution (prepared by mixing 1 mL of acetic acid in 1000 mL of distilled water):acetonitrile=75:25
Detection: UV 220 nm
Flow rate: about 1.0 mL/min
Column temperature: constant temperature at around 40° C.
Measurement time: about 25 min
Injection volume: 5 μL
The diastereomeric excess was calculated according to the following formula using the peak area ratios of the title compound (retention time: about 14.5 min) and the R form (retention time: about 15.5 min).

% de={[(the peak area ratio of the title compound (S form))−(the peak area ratio of the R form)]÷ [(the peak area ratio of the title compound (S form))+(the peak area ratio of the R form)]}× 100

When various examinations were performed for the systems in which a crystal (a diastereomer salt) was obtained using the above-mentioned amines, quinine and quinidine gave a diastereomer salt having a desired absolute configuration (S form), and cinchonidine gave a diastereomer salt having an opposite absolute configuration (R form). The main results are shown in Table 4.

Hereinafter, in the table, EtOAc represents ethyl acetate, CH₃CN represents acetonitrile, and DME represents dimethoxyethane.

TABLE 4

| | Amine | Solvent (amount of solvent) | Temperature ° C. | % de | Yield % |
|---|---|---|---|---|---|
| 1 | Quinine | EtOAc (0.2 ml) | Filtration at room temperature | 69 (S form) | 43.7 |
| 2 | | EtOAc (0.3 ml) | 50 → 20 | 90 (S form) | 42.5 |
| 3 | | CH₃CN (0.3 ml) | 50 → 20 | 79 (S form) | 45.2 |
| 4 | | Acetone (0.3 ml) | 50 → 20 | 95 (S form) | 43.5 |
| 5 | | DME (0.3 ml) | 50 → 20 | 91 (S form) | 39.5 |
| 6 | Cinchonidine | EtOAc (0.3 ml) | 50 → 20 | 88 (R form) | 33.4 |
| 7 | Quinidine | CH₃CN-water (about 0.3 ml) | 50 → 20 | 58 (S form) | 44.5 |
| 8 | | acetone-water (about 0.3 ml) | 50 → 20 | 60 (S form) | 44.0 |
| 9 | | DME-water (about 0.3 ml) | 50 → 20 | 59 (S form) | 48.9 |

When optical resolution was performed in the same manner using (R)-(−)-α-phenylglycitol, (S)-(−)-N,N-dimethyl-1-phenyl-ethylmine, L-lysine, and the like, the diastereomeric excess was 5% de or less.

Next, the number of equivalents of amine was examined for the purpose of improving the amount of diastereomer. The results of the examination are shown in Table 5.

TABLE 5

| Entry | Amine | Number of equivalents | Solvent | Temperature ° C. | % de | Yield % |
|---|---|---|---|---|---|---|
| 1 | Quinine | 0.45 | Acetone (0.3 ml) | 50 → 20 | 94 (S form) | 39.4 |
| 2 | | 0.50 | | | 95 (S form) | 43.5 |
| 3 | | 0.55 | | | 93 (S form) | 43.5 |
| 4 | Quinidine | 0.45 | EtOAc (0.3 ml) | 50 → 20 | 92 (R form) | 32.1 |
| 5 | | 0.50 | | | 88 (R form) | 33.4 |

Based on the above results, quinine gave a diastereomer having a desired absolute configuration (S form), and cinchonidine gave a diastereomer salt having an opposite absolute configuration (R form) with high purity in medium to high yield.

Example 10

Production of (S)-1-(2-hydroxyethyl)-4-methyl-5-[2-(trifluoromethyl)phenyl]-1H-pyrrole-3-carboxylic acid quinine salt by racemization of (R)-1-(2-hydroxyethyl)-4-methyl-5-[2-(trifluoromethyl)phenyl]-1H-pyrrole-3-carboxylic acid

(10-1) Production of (S)-1-(2-hydroxyethyl)-4-methyl-5-[2-(trifluoromethyl)phenyl]-1H-pyrrole-3-carboxylic acid quinine salt by racemization of (R)-1-(2-hydroxyethyl)-4-methyl-5-[2-(trifluoromethyl)phenyl]-1H-pyrrole-3-carboxylic acid The filter washing liquid (583.63 g, content of (R)-1-(2-hydroxyethyl)-4-methyl-5-[2-(trifluoromethyl)phenyl]-1H-pyrrole-3-carboxylic acid and (S)-1-(2-hydroxyethyl)-4-methyl-5-[2-(trifluoromethyl)phenyl]-1H-pyrrole-3-carboxyl is acid: 22.23 g) obtained by the optical resolution method of (RS)-1-(2-hydroxyethyl)-4-methyl-5-[2-(trifluoromethyl)phenyl]-1H-pyrrole-3-carboxylic acid described in (Example 7) was concentrated under reduced pressure (75.73 g). The obtained concentrated liquid was heated to 140 to 150° C. and stirred for about 5 hours, and thereafter cooled and concentrated under reduced pressure (Reaction Solution 1, 40 mL).

After ethyl acetate (220 mL), water (7.3 mL), and quinine (19.18 g (59 mmol)) were mixed at room temperature, Reaction Solution 1 was added thereto at the same temperature. The resulting mixture was heated to about 65° C., and thereafter gradually cooled to 0 to 5° C. (cooling rate as a guide: about 0.3° C./min) and stirred for about 1 hour at that temperature. The resulting crystal was filtered and washed with ethyl acetate (40 mL) cooled to 0 to 5° C., and the obtained wet crystal product was dried under reduced pressure at 40° C., whereby (S)-1-(2-hydroxyethyl)-4-methyl-5-[2-(trifluoromethyl)phenyl]-1H-pyrrole-3-carboxylic acid quinine salt (19.59 g) was obtained (yield: 43.3%). The diastereomeric excess of the obtained salt was determined by using the method of (Example 7-2) and found to be 94.8% de.

(10-2-1) Racemization of (R)-1-(2-hydroxyethyl)-4-methyl-5 [2-(trifluoromethyl)phenyl]-1H-pyrrole-3-carboxylic acid The filter washing liquid obtained by the optical resolution method of (RS)-1-(2-hydroxyethyl)-4-methyl-5-[2-(trifluoromethyl)phenyl]-1H-pyrrole-3-carboxylic acid described in (Example 7) was concentrated under reduced pressure. To the residue (15.46 g) (a foam shape, R form, 84.6% ee, Net 14.38 g), N,N-dimethylformamide (77 mL) was added, and the resulting mixture was heated to 140 to 145° C. and stirred for about 6 hours. Then, the mixture was cooled to room temperature, and water (77 mL) and toluene (464 mL) were added thereto to effect extraction, and the obtained organic layer was washed three times with water (77 mL). The washed organic layer was concentrated under reduced pressure (155 mL) and cooled to 0 to 5° C. and stirred for about 1 hour at that temperature. The resulting crystal was filtered and washed with toluene (31 mL) cooled to 0 to 5° C. The obtained wet crystal product was dried under reduced pressure at 40° C., whereby (RS)-1-(2-hydroxyethyl)-4-methyl-5-[2-(trifluoromethyl)phenyl]-1H-pyrrole-3-carboxylic acid was obtained (10.70 g, content: 95.2% (Net 10.19 g), 0.5% ee, yield: 70.9%). The content was determined by using the method described in (10-2-2).

By using the obtained (RS)-1-(2-hydroxyethyl)-4-methyl-5-[2-(trifluoromethyl)phenyl]-1H-pyrrole-3-carboxylic acid as a starting material, and also using the method described in Example 7, (S)-1-(2-hydroxyethyl)-4-methyl-5-[2-(trifluoromethyl)phenyl]-1H-pyrrole-3-carboxylic acid quinine salt can be produced.

(10-2-2) HPLC Determination Method for Content

About 25 mg of (R)-1-(2-hydroxyethyl)-4-methyl-5-[2-(trifluoromethyl)phenyl]-1H-pyrrole-3-carboxylic acid was collected and diluted with a mobile phase to 50 mL, whereby a standard solution or a sample solution was prepared.
Column: L-column C8 (4.6 mm I.D.×250 mm, 5 μm) available from Chemicals Evaluation and Research Institute
Mobile Phase:
Solution A: acetonitrile:a 5 mM aqueous disodium hydrogen phosphate solution=20:80
Solution B: acetonitrile:water=80:20
The gradient composition is shown in Table 6.

TABLE 6

| Time (min) | 0-5 | 5-15 | 15-30 |
|---|---|---|---|
| Solution A:Solution B | 85:15 | 85:15 → 0:100 | 0:100 |

Detection: UV 254 nm
Flow rate: about 1.0 mL/min
Column temperature: constant temperature at around 40° C.
Measurement time: about 30 min
Injection volume: 5 μL The content was calculated according to the following formula using the peak area of the title compound (retention time: about 6.5 min) (absolute calibration curve method).

Content (%)=$F \times (Ws \div Wt) \times (Qt \div Qs)$

Ws: weight of reference standard (mg), Wt: weight of unknown sample (mg), Qs: peak area of standard solution, Qt: peak area of sample solution, F: content of reference standard (%)

Example 11

(R)-1-(2-Hydroxyethyl)-4-methyl-5-[2-(trifluoromethyl)phenyl]-1H-pyrrole-3-carboxylic acid cinchonidine salt To cinchonidine (46.98 g (159.6 mmol)), ethyl acetate (1400 mL) was added, and while heating and stirring the resulting mixture under reflux (about 78° C.), (RS)-1-(2-hydroxyethyl)-4-methyl-5-[2-(trifluoromethyl)phenyl]-1H-pyrrole-3-carboxylic acid (50.00 g (159.6 mmol)) was added thereto. The resulting mixture was stirred for about 1 hour, and then gradually cooled to 20 to 30° C., and further stirred for about 1 hour at that temperature. The deposited crystal was filtered and washed with ethyl acetate (250 mL). The obtained wet crystal product was dried under reduced pressure at 40° C., whereby a crude product of the title compound (52.73 g) was obtained (yield: 54.4%). The diastereomeric excess of the obtained salt was 71.9% de.

To the obtained crude product (50.00 g), ethanol (75 mL) and ethyl acetate (100 mL) were added, and the resulting mixture was heated and stirred under reflux (about 78° C.). After the mixture was stirred for about 1 hour, ethyl acetate (825 mL) was added thereto, and the resulting mixture was stirred under reflux again for about 0.5 hours. Thereafter, the mixture was cooled to 0 to 5° C. and stirred for about 1 hour at that temperature. The resulting crystal was filtered and washed with ethyl acetate (200 mL) cooled to 0 to 5° C. The obtained wet crystal product was dried under reduced pressure at 40° C., whereby the title compound was obtained (34.21 g, recovery rate: 68.4%, yield: 37.2%). The diastereomeric excess of the obtained salt was 98.7% de.

$^1$H NMR (400 MHz, CDCl$_3$) δ: 1.27-1.67 (m, 2H), 1.75-2.04 (m, 4H), 2.13-2.33 (m, 1H), 2.52-2.94 (m, 2H), 3.14-3.23 (m, 2H), 3.46-4.12 (m, 2H), 4.76-5.10 (m, 2H), 5.58-5.90 (m, 2H), 6.10-6.95 (m, 2H), 7.00-8.25 (m, 7H), 8.55-9.01 (m, 1H). MS (ESI): 313, 294

Example 12

Production method (2) for (S)-1-(2-hydroxyethyl)-4-methyl-N-[4-(methylsulfonyl)phenyl]-5-[2-(trifluoromethyl)phenyl]-1H-pyrrole-3-carboxamide (Compound (A))

(12-1) (S)-1-(2-Hydroxyethyl)-4-methyl-5-[2-(trifluoromethyl)phenyl]-1H-pyrrole-3-carboxylic acid To (S)-1-(2-hydroxyethyl)-4-methyl-5-[2-(trifluoromethyl)phenyl]-1H-pyrrole-3-carboxylic acid (8α,9R)-6'-methoxycinchonan-9-ol (10.00 g (16 mmol)) obtained by the production method of Example 7, t-butyl methyl ether (90 mL), water (10 mL), and a 36 w/w % aqueous hydrochloric acid solution (5 mL) were added, and the resulting mixture was stirred at room temperature, followed by liquid separation. The obtained organic layer was concentrated under reduced pressure (30 mL), and ethyl acetate (50 mL) was added thereto, and the resulting mixture was further concentrated under reduced pressure, whereby a solution containing the title compound (30 mL) was obtained.

(12-2) 2-((S)-3-Methyl-4-{[4-(methylsulfonyl)phenyl]carbamoyl}-2-[2-(trifluoromethyl)phenyl]-1H-pyrrol-1-yl)ethyl N-{[4-(methylsulfonyl)phenyl]amino}oxamate Ethyl acetate (50 mL), tetrahydrofuran (20 mL), and oxalyl chloride (5.18 g (41 mmol)) were mixed, and the resulting mixture was cooled to 0 to 5° C. Then, the solution obtained in Example (12-1) was added thereto while maintaining the temperature at 0 to 5° C., and the resulting mixture was stirred at 0 to 10° C. for 6 hours. After stirring, acetonitrile (30 mL) and pyridine (0.62 g (8 mmol)) were added thereto, and the reaction solution was concentrated under reduced pressure (30 mL), and acetonitrile (50 mL) was added thereto, and the resulting mixture was further concentrated under reduced pressure (30 mL).

After completion of concentration under reduced pressure, acetonitrile (10 mL) and oxalyl chloride (0.10 g (1 mmol)) were added thereto, and the resulting mixture was cooled to 0 to 5° C. (Reaction Solution 1).

After acetonitrile (30 mL), pyridine (3.15 g (40 mmol)), and 4-(methylsulfonyl)aniline (6.71 g (39 mmol)) were sequentially added, Reaction Solution 1 was added thereto while maintaining the temperature at 10 to 15° C., and the resulting mixture was heated to 20 to 25° C. and stirred for about 1 hour.

Insoluble matter was filtered from the obtained reaction solution and washed with acetonitrile (10 mL), and then water (15 mL) was added thereto, and the resulting mixture was stirred for about 2 hours. Then, water (75 mL) was added dropwise thereto over about 1 hour. After the resulting suspension was stirred for about 1 hour, the crystal was filtered and washed with a 50 v/v % aqueous acetonitrile solution (20 mL), whereby a wet product of the title compound (undried product, 15.78 g) was obtained $^1$H NMR (500 MHz, DMSO-d$_6$) δ: 1.94 (s, 3H), 3.19 (s, 3H), 3.20 (s, 3H), 3.81 (t, 1H), 4.12 (t, 1H), 4.45 (t, 2H, J=5.81 Hz), 7.62 (t, 1H, J=4.39 Hz), 7.74 (t, 2H, J=3.68 Hz), 7.86 (dd, 3H), 7.92 (dd, 3H, J=6.94, 2.13 Hz), 7.97 (dd, 2H, J=6.80, 1.98 Hz), 8.02 (dd, 2H), 10.03 (s, 1H), 11.19 (s, 1H)

(12-3) (S)-1-(2-Hydroxyethyl)-4-methyl-N-[4-(methylsulfonyl)phenyl]-5-[2-(trifluoromethyl)phenyl]-1H-pyrrole-3-carboxamide (Compound (A))

To the crystal of the wet product obtained in (12-2), t-butyl methyl ether (50 mL), acetonitrile (10 mL), a 48 w/w aqueous potassium hydroxide solution (4 g), and water (50 mL) were added, and the resulting mixture was stirred at 15 to 25° C. for about 2 hours. After stirring, liquid separation was performed, and the obtained organic layer was concentrated under reduced pressure (30 mL), and ethanol (60 mL) was added thereto, and the resulting mixture was further concentrated under reduced pressure (30 mL). After completion of concentration under reduced pressure, ethanol (14 mL) and water (20 mL) were added thereto, and then, a seed crystal was added thereto to deposit a crystal. After water (50 mL) was added dropwise thereto over about 1 hour, the resulting mixture was stirred for about 1 hour, and the resulting crystal was filtered. Thereafter, the crystal was washed with a 30 v/v % aqueous ethanol solution (10 mL) and dried under reduced pressure at 40° C., whereby the title compound was obtained in the form of a crystal (6.36 g, yield: 87.0%). The amount of enantiomer of the obtained crystal was 0.05%. The amount of enantiomer was determined by the method described in (Example 8-4).

$^1$H NMR (400 MHz, CDCl$_3$) δ: 1.74 (1H, broad singlet), 2.08 (3H, s), 3.04 (3H, s), 3.63-3.80 (4H, m), 7.36 (1H, d, J=7.2 Hz), 7.48 (1H, s), 7.58-7.67 (2H, m), 7.77-7.90 (6H, m)

Example 13

Ethyl (RS)-2-chloro-1-(2-hydroxyethyl)-4-methyl-5-[2-(trifluoromethyl)phenyl]-1H-pyrrole-3-carboxylate

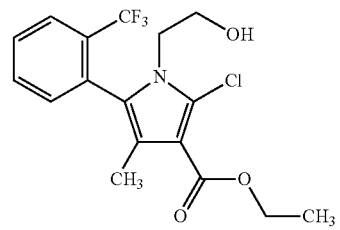 [SMILES: CCOC(=O)c1c(C)c(-c2ccccc2C(F)(F)F)n(CCO)c1Cl]

To ethyl 2-chloro-4-methyl-5-[2-(trifluoromethyl)phenyl]-1H-pyrrole-3-carboxylate (40.01 g (121 mmol)) obtained by the production method of Example 3, ethylene carbonate (13.82 g (157 mmol)), 4-dimethylaminopyridine (1.50 g (12.2 mmol)), and N,N-dimethylacetamide (80 mL) were sequentially added at room temperature, and the resulting mixture was heated to 105 to 120° C. and stirred. After about 3 hours, the mixture was cooled to 10° C. to 25° C., and toluene (600 mL), water (180 mL), and concentrated hydrochloric acid (60 mL) were added thereto, and the organic layer was extracted. Then, to the organic layer, water (200 mL) was added to wash the organic layer (washing was performed twice). The obtained organic layer was concentrated under reduced pressure, and ethanol (400 mL) was added thereto, and the resulting mixture was concentrated under reduced pressure, whereby an ethanol solution of the title compound (about 120 mL) was obtained.

1H-NMR (500 MHz, CDCl3) δ: 1.36 (dt, 4H, J=11.99, 5.08 Hz), 1.55 (s, 1H), 1.93 (s, 3H), 3.66 (dtt, 3H, J=40.62, 12.53, 4.65 Hz), 3.95-4.00 (m, 1H), 4.30 (q, 2H, J=7.19 Hz), 7.36 (t, 1H, J=3.72 Hz), 7.59 (ddd, 2H, J=20.65, 9.24, 5.27 Hz), 7.78 (d, 1H, J=7.69 Hz)

Example 14

Ethyl (RS)-1-(2-hydroxyethyl)-4-methyl-5-[2-(trifluoromethyl)phenyl]-1H-pyrrole-3-carboxylate

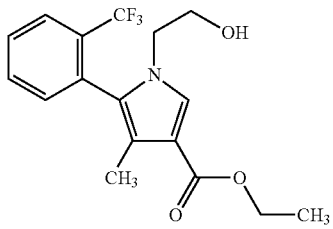 [SMILES: CCOC(=O)c1cn(CCO)c(-c2ccccc2C(F)(F)F)c1C]

To the ethyl (RS)-2-chloro-1-(2-hydroxyethyl)-4-methyl-5-[2-(trifluoromethyl)phenyl]-1H-pyrrole-3-carboxylate/ethanol solution (about 120 mL) obtained by the production method of Example 13, ethanol (160 mL), sodium formate (10.68 g (157 mmol)), a 5% palladium-carbon catalyst (water content: 56.8%, 4.61 g), and water (20 mL) were added at room temperature, and the resulting mixture was heated to 55° C. to 65° C. and stirred. After the mixture was stirred for about 2.5 hours, the mixture was cooled to 15° C. to 25° C. Thereafter, a filter aid (KC Flock, Nippon Paper Industries) (2.03 g) was added thereto, and the catalyst was filtered, and then, the residue was washed with ethanol (160 mL). After concentration under reduced pressure, an ethanol solution of the title compound (about 200 mL) was obtained.

1H NMR (400 MHz, CDCl$_3$) δ: 1.35 (3H, t, J=7.1 Hz), 1.84 (1H, broad singlet), 2.00 (3H, s), 3.63-3.77 (4H, m), 4.27 (2H, m), 7.35-7.79 (5H, m).

Example 15

(RS)-1-(2-hydroxyethyl)-4-methyl-5-[2-(trifluoromethyl)phenyl]-1H-pyrrole-3-carboxylic acid

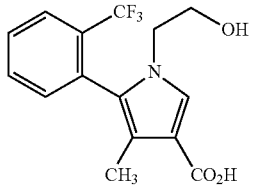 [SMILES: Cc1c(C(=O)O)cn(CCO)c1-c1ccccc1C(F)(F)F]

To the ethyl (RS)-1-(2-hydroxyethyl)-4-methyl-5-[2-(trifluoromethyl)phenyl]-1H-pyrrole-3-carboxylate/ethanol solution (about 200 mL) obtained by the production method of Example 14, water (80 mL) and sodium hydroxide (11.55 g (289 mmol)) were added at room temperature, and the resulting mixture was heated to reflux. After the mixture was stirred for about 5 hours, the mixture was cooled to room temperature, and water (264 mL) was added thereto, and then, the pH of the mixture was adjusted to 5 to 6 with concentrated hydrochloric acid. After the mixture was stirred for about 40 minutes, the mixture was cooled to 10° C. or lower, and again, the pH of the mixture was adjusted to 3 to 4 with concentrated hydrochloric acid. After the mixture was stirred for 2 to 3 hours, the deposited crystal was filtered and washed with a cooled 20% aqueous ethanol solution (120 mL). The obtained wet crystal product was dried under reduced pressure at 40° C., whereby the title compound was obtained (36.87 g, yield: 97.6%).

1H-NMR (CDCl$_3$) δ: 2.00 (s, 3H), 3.62-3.77 (m, 4H), 7.34 (d, 1H, J=7.44 Hz), 7.59 (dt, 3H, J=25.63, 6.57 Hz), 7.78 (d, 1H, J=7.69 Hz).

Formulation Example 1

Capsule

The crystal (5 g) obtained in Example 8, lactose (115 g), cornstarch (58 g) and magnesium stearate (2 g) are mixed using a V-type mixer, and the resulting mixture is filled in a capsule (180 mg per capsule), whereby a capsule is obtained.

Formulation Example 2

Tablet

The crystal (5 g) obtained in Example 8, lactose (90 g), cornstarch (34 g), crystalline cellulose (20 g), and magnesium stearate (1 g) are mixed using a V-type mixer, and the resulting mixture is tableted (a mass of 150 mg per tablet) using a tableting machine, whereby a tablet is obtained.

Formulation Example 3

Suspension

A dispersion medium in which methyl cellulose is dispersed or dissolved in purified water is prepared. The crystal obtained in Example 8 is weighed and placed in a mortar and kneaded well while adding the above-mentioned dispersion medium thereto in small portions, and then, purified water is added thereto, whereby a suspension (100 g) is prepared.

The invention claimed is:

1. A method for resolving a compound represented by the following general formula (I):

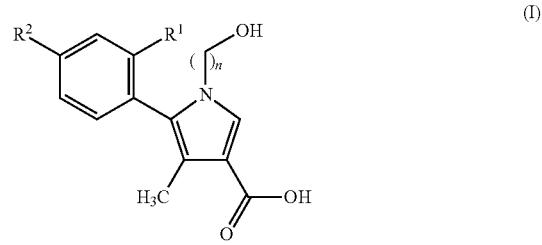

[wherein R$^1$ represents a methyl group or a trifluoromethyl group, R$^2$ represents a hydrogen atom or a C1-C3 alkoxy group, and n represents an integer selected from 1 to 3] into its atropisomers, comprising stirring the compound with an optically active amine having a cinchonine skeletal formula.

2. The method according to claim 1, wherein the optically active amine is one compound selected from the group of compounds represented by the following formulae:

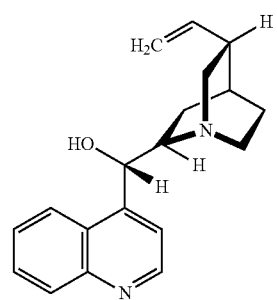

Cinchonine

-continued

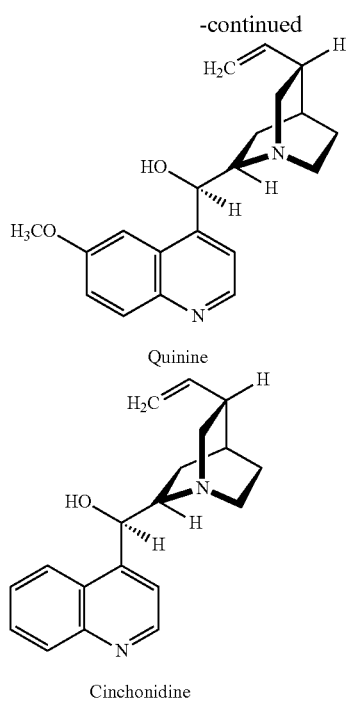

Quinine

Cinchonidine

Quinidine

3. The method according to claim 1, wherein the optically active amine is quinine represented by the following formula:

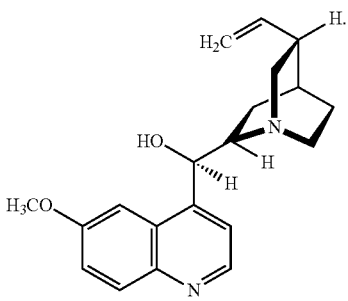

4. The method according to claim 1, wherein the method is performed in an organic solvent or a mixed solvent of an organic solvent and water.

5. The method according to claim 1, wherein the compound represented by the general formula (I) is the following compound (Ia):

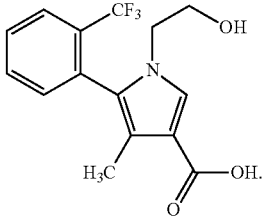

(Ia)

* * * * *